(12) United States Patent
Hubschwerlen et al.

(10) Patent No.: US 8,415,375 B2
(45) Date of Patent: Apr. 9, 2013

(54) 2-HYDROXYETHYL-1H-QUINOLIN-2-ONE DERIVATIVES AND THEIR AZAISOSTERIC ANALOGUES WITH ANTIBACTERIAL ACTIVITY

(75) Inventors: Christian Hubschwerlen, Durmenach (FR); Georg Rueedi, Allschwil (CH); Jean-Philippe Surivet, Kembs (FR); Cornelia Zumbrunn Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/263,922

(22) PCT Filed: Apr. 8, 2010

(86) PCT No.: PCT/IB2010/051517
§ 371 (c)(1), (2), (4) Date: Oct. 11, 2011

(87) PCT Pub. No.: WO2010/116337
PCT Pub. Date: Oct. 14, 2010

(65) Prior Publication Data
US 2012/0040989 A1   Feb. 16, 2012

(30) Foreign Application Priority Data
Apr. 9, 2009   (WO) .................. PCT/IB2009/051510

(51) Int. Cl.
*A01N 43/42*   (2006.01)
*A61K 31/47*   (2006.01)

(52) U.S. Cl.
USPC .......................................... 514/312; 546/122

(58) Field of Classification Search .................. 546/122; 514/299, 311, 312
See application file for complete search history.

(56) References Cited

U.S. PATENT DOCUMENTS

| 8,211,890 B2 | 7/2012 | Hubschwerlen et al. |
| 2010/0331308 A1 | 12/2010 | Hubschwerlen et al. |
| 2011/0082132 A1 | 4/2011 | Hubschwerlen et al. |
| 2011/0201595 A1 | 8/2011 | Hubschwerlen et al. |

FOREIGN PATENT DOCUMENTS

| EP | 1900732 | 3/2008 |
| WO | WO 2006/002047 | 1/2006 |
| WO | WO 2006/032466 | 3/2006 |
| WO | WO 2006/134378 | 12/2006 |
| WO | WO 2006/137485 | 12/2006 |
| WO | WO 2007/138974 | 12/2007 |
| WO | WO 2008/009700 | 1/2008 |
| WO | WO 2008/071961 | 6/2008 |
| WO | WO 2008/071962 | 6/2008 |
| WO | WO 2008/071964 | 6/2008 |
| WO | WO 2008/071981 | 6/2008 |
| WO | WO 2008/128942 | 10/2008 |
| WO | WO 2009/000745 | 12/2008 |
| WO | WO 2009/001126 | 12/2008 |
| WO | WO 2009/087153 | 7/2009 |
| WO | WO 2009/104159 | 8/2009 |
| WO | WO 2009/147616 | 12/2009 |
| WO | WO 2010/411218 | 4/2010 |
| WO | WO 2010/067332 | 6/2010 |
| WO | WO 2010/116337 | 10/2010 |

OTHER PUBLICATIONS

Turner; "A general approach to the synthesis of 1,6-, 1,7-, and 1,8-Naphthyridines"; J. Org. Chem., vol. 55, pp. 4744-4750; 1990.
Corey, et al.; "Highly enantioselective borane reduction of ketones catalyzed by chiral oxazaborolidines. Mechanism and synthetic implications.;" J. Am. Cehm. Soc., vol. 109, pp. 5551-5553; 1987.
Wikler, et al.; "Methods for dilution antimicrobial susceptibility tests for bacteria that grow aerobically; approved standard—seventh edition;" Clinical and Laboratory Standards Institute, vol. 26, No. 2; A7-A7; ISBN 1-56238-587-9; ISSN 0273-3099; 2006.
Greene; "Protection for the Amino Group"; P.G.M. Wuts, Wiley-Interscience, pp. 494-496; 1999.
Shi; "Organocatalytic asymmetric epoxidation of olefins by chiral ketones;" Acc. Chem. Res., vol. 37, pp. 488-496; 2004.
Brown, et al.; "Chiral synthesis via organoboranes. 22. Selective reductions. 44. The effect of the steric requirements of the alkyl substituent in isopinocampheylalkylchloroboranes for the asymmetric reduction of representative ketones;" J. Org. Chem., vol. 54, pp. 1577-1583; 1989.
Kolb, et al.; "Catalytic asymmetric dihydroxylation;" Chem. Rev., vol. 94, No. 8, pp. 2483-2547; 1994.
Talbot, et al.; "Bad bugs need drugs: an update on the development pipeline from the antimicrobial availability task force of the infectious diseases society of America;" Anti-Infective Development Pipeline; CID, vol. 42, pp. 657-668; Mar. 1, 2006.

(Continued)

*Primary Examiner* — Paul V. Ward
(74) *Attorney, Agent, or Firm* — Hunton & Williams LLP

(57) ABSTRACT

The invention relates to antibacterial compounds of formula I

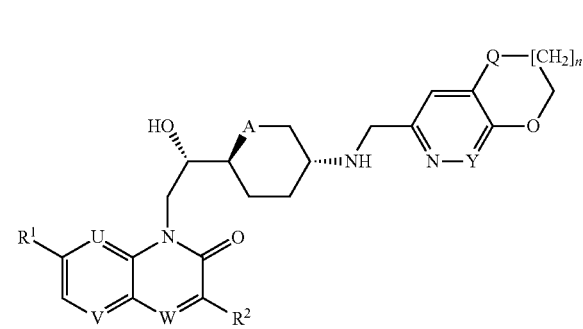

wherein
$R^1$ represents alkoxy;
each of U and V represents CH and W represents CH or N, or
U represents N, V represents CH and W represents N, or
each of U and V represents N and W represents CH;
$R^2$ represents hydrogen or fluorine when W represents CH or $R^2$ represents hydrogen when W represents N;
A represents O or $CH_2$;
Y represents CH or N;
Q represents O or S; and
n represents 0 or 1;
and salts of such compounds.

12 Claims, No Drawings

OTHER PUBLICATIONS

Mancuso, et al.; "Oxidation of long-chain and related alcohols to carbonyls by dimethyl sulfoxide "activated" by oxalyl chloride;" The Journal of Organic Chemistry, Vo. 43, No. 12, pp. 2480-2482; 1978.

Dess, et al.; "Readily accessible 12-1-5 oxidant for the conversion of primary and secondary alcohols to aldehydes and ketones;" Journal of Organic Chemistry, vol. 48, No. 22, pp. 4155-4156; 1983.

Greene, et al.; "Protective groups in organic synthesis—Third edition"; 1999.

Gould; "Salt selection for basic drugs;" International Journal of Pharmaceuticals, vol. 33, pp. 201-217; 1986.

Noyori, et al.; "Rational designing of efficient chiral reducing agents. Highly enantioselective reduction of aromatic ketones by binaphthol-modified lithium aluminum hydride reagents;" J. Am. Chem. Soc., vol. 106, pp. 6709-6716; 1984.

Ferrarini, et al.; "Synthesis of 1,8-naphthyridine derivatives. Potential antihypertensive agents.;" J. Heterocyclic Chem., vol. 23, pp. 501-504; 1986.

Schaus, et al.; "Highly selective hydrolytic kinetic resolution of terminal epoxides catalyzed by chiral (salen)$Co^{III}$ complexes. Practical synthesis of enantioenriched terminal epoxides and 1,2-diols;" J. Am. Chem. Soc., vol. 124, No. 7, pp. 1307-1315; 2002.

Remington "The science and practice of pharmacy" $21^{st}$ edition; Part 5, "Pharmaceutical Manufacturing"; 2005.

Tokunaga, et al.; "Asymmetric catalysis with water: efficient kinetic resolution of terminal epoxides by means of catalytic hydrolysis;" Science, vol. 277, pp. 936-938; 1997.

Kolb, et al.; "A simplified procedure for the stereospecific transformation of 1,2-diols into epoxides;" Tetrahedron, vol. 48, No. 48, pp. 105-10530; 1992.

Sato, et al.; "One-pot reductive amination of aldehydes and ketones with α-picoline-borane in methanol, in water, and in neat conditions;" Tetrahedron, vol. 60, pp. 7899-7906, 2004.

Noyori, et al.; "Asymmetric transfer hydrogenation catalyzed by chiral ruthenium complexes;" Acc. Chem. Res., vol. 30, pp. 97-102; 1997.

Larock; "Comprehensive organic transformations;" A Guide to Functional Group Preparations, Second Edition; pp. 1075-1111; Published by Wiley-Vch; 1999.

2-HYDROXYETHYL-1H-QUINOLIN-2-ONE DERIVATIVES AND THEIR AZAISOSTERIC ANALOGUES WITH ANTIBACTERIAL ACTIVITY

CROSS-REFERENCE TO RELATED APPLICATIONS

This application is the national phase application of PCT/IB2010/051517, filed Apr. 8, 2010, which claims the benefit of PCT/IB2009/051510, filed Apr. 9, 2009, the contents of each are hereby incorporated by reference in their entirety.

FIELD OF THE INVENTION

The present invention concerns 2-hydroxyethyl-1H-quinolin-2-one antibiotic compounds and their azaisoteric analogues, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

BRIEF SUMMARY OF THE INVENTION

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

*S. aureus* is resistant to β-lactams, quinolones and now even to vancomycin;

*S. pneumoniae* is becoming resistant to penicillin or quinolone antibiotics and even to new macrolides;

*Enteroccocci* are quinolone and vancomycin resistant and β-lactam antibiotics are inefficacious against these strains;

*Enterobacteriacea* are cephalosporin and quinolone resistant;

*P. aeruginosa* are β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella species* and *Pseudomonas aeruginosa* (*Clinical Infectious Diseases* (2006), 42, 657-68).

In addition, microorganisms that are causing persistent infections are increasingly being recognized as causative agents or cofactors of severe chronic diseases like peptic ulcers or heart diseases.

WO 2006/134378 describes notably antibacterial compounds of formulae (A1) and (A2)

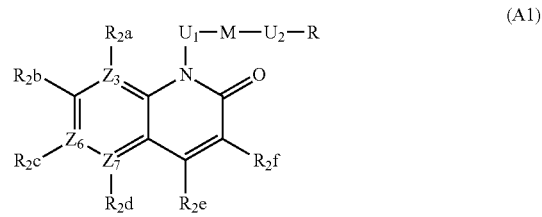

(A1)

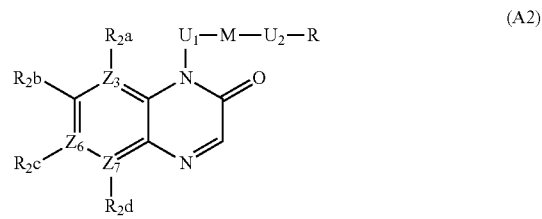

(A2)

wherein $Z_3$, $Z_6$ and $Z_7$ are C or N provided that when $Z_3$, $Z_6$ or $Z_7$ is N then $R_2a$, $R_2c$ or $R_2d$ is absent;

$R_2a$, $R_2b$, $R_2c$ and $R_2d$ may each independently represent (notably) H, fluoro, chloro or ($C_1$-$C_6$)alkoxy;

$U_1$ may represent CRaRb-CRcRd wherein Ra, Rb, Rc and Rd may each independently represent H or ($C_1$-$C_6$)alkyl;

M may notably represent the group

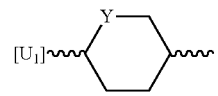

wherein Y may notably be $CH_2$ or O;

$U_2$ may notably represent NH—$CH_2$;

R may notably represent aryl or heteroaryl which may be optionally substituted on carbon; and any of $U_1$, M, $U_2$ and R may optionally be substituted on carbon by one to three substituents selected from (notably) halo, hydroxy, oxo or amino.

However WO 2006/134378 does not specifically disclose any compounds having an hydroxy group attached to the $U_1$ radical.

WO 2006/137485, WO 2007/138974, WO 2008/009700, WO 2008/071961, WO 2008/071962, WO 2008/071964, WO 2008/071981 and WO 2009/001126 describe similar antibacterial compounds based on a 1H-quinolin-2-one, 1H-quinoxalin-2-one, 1H-[1,8]naphthyridin-2-one, 1H-[1,5]naphthyridin-2-one or 4H-pyrido[2,3-b]pyrazin-3-one motif. Again, no compounds of this type having an hydroxy group attached to the middle chain are described in these documents.

The instant invention provides further antibacterial compounds based on a 1H-quinolin-2-one, 1H-quinoxalin-2-one, 1H-[1,8]naphthyridin-2-one or 4H-pyrido[2,3-b]pyrazin-3-one motif. The Applicants have found that such compounds have antibacterial properties combined with a low hERG $K^+$ channel inhibition, which makes them less likely to prolong the QT interval and to bring about ventricular dysrhythmia.

DETAILED DESCRIPTION OF PREFERRED EMBODIMENTS

Various embodiments of the invention are presented hereafter:

i) The invention firstly relates to compounds of formula I

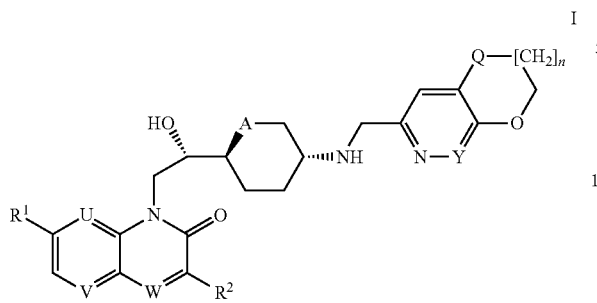

wherein
R¹ represents alkoxy (notably methoxy);
each of U and V represents CH and W represents CH or N, or
U represents N, V represents CH and W represents CH or N (notably N), or
each of U and V represents N and W represents CH;
R² represents hydrogen or fluorine when W represents CH or R² represents hydrogen when
W represents N;
A represents O or CH$_2$;
Y represents CH or N;
Q represents O or S; and
n represents 0 or 1;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "(C$_1$-C$_x$)alkyl" (x being an integer) refers to a straight or branched chain alkyl group containing 1 to x carbon atoms. For example, a (C$_1$-C$_4$)alkyl group contains from one to four carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "alkoxy", used alone or in combination, refers to a straight or branched chain alkoxy group containing from one to four carbon atoms. The term "(C$_x$-C$_y$)alkoxy" (x and y each being an integer) refers to an alkoxy group as defined before containing x to y carbon atoms. For example, a (C$_1$-C$_3$)alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "halogen" refers to fluorine, chlorine, bromine or iodine, and preferably to fluorine or chlorine.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

In this text, a bond interrupted by a wavy line shows a point of attachment of the radical drawn to the rest of the molecule. For example, the radical drawn below

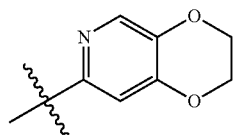 [SMILES: *c1cc2c(cn1)OCCO2]

is the 2,3-dihydro-[1,4]dioxino[2,3-c]pyridine-7-yl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention notably relates to compounds of formula I that are also compounds of formula I$_p$

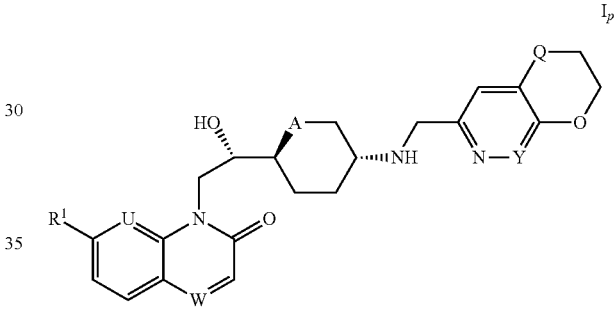

wherein
R¹ represents alkoxy (notably methoxy);
U and W each independently represent CH or N;
A represents O or CH$_2$;
Y represents CH or N; and
Q represents O or S;
and to salts (in particular pharmaceutically acceptable salts) of compounds of formula I$_p$.

iii) According to one main embodiment of this invention, the compounds of formula I as defined in embodiment i) or ii) will be such that Y represents CH.

iv) According to another main embodiment of this invention, the compounds of formula I as defined in embodiment i) or ii) will be such that Y represents N.

v) A further embodiment of this invention relates to the compounds of formula I as defined in one of embodiments i) to iv) wherein Q represents O.

vi) One sub-embodiment of embodiment v) relates to the compounds of formula I as defined in embodiment i) wherein:
Q represents O;
R¹ represents methoxy;
U represents N and either V represents CH and W represents N or V represents N and W represents CH;
R² represents hydrogen;
A represents O or CH$_2$ (and preferably O);
Y represents CH; and
n represents 1.

vii) Yet a further embodiment of this invention relates to the compounds of formula I as defined in one of embodiments i) to iv) wherein Q represents S.

viii) One sub-embodiment of embodiment vii) relates to the compounds of formula I as defined in embodiment i) wherein:
Q represents S;
$R^1$ represents methoxy;
U represents N and either V represents CH and W represents N or V represents N and W represents CH;
$R^2$ represents hydrogen;
A represents O or $CH_2$ (and preferably O);
Y represents CH; and
n represents 1.

ix) The invention relates in particular to compounds of formula I as defined in one of embodiments i) to viii) above wherein V, if present, represents CH and U represents N and W represents CH, or U represents CH and W represents N, or also each of U and W represents N.

x) One sub-embodiment of embodiment ix) relates to the compounds of formula I as defined in embodiment vi) wherein U represents N and W represents CH.

xi) Another sub-embodiment of embodiment ix) relates to the compounds of formula I as defined in embodiment vi) wherein U represents CH and W represents N.

xii) Yet another sub-embodiment of embodiment ix) relates to the compounds of formula I as defined in embodiment vi) wherein each of U and W represents N.

xiii) The invention also relates to compounds of formula I as defined in embodiment i) or as defined in embodiment i) taken in combination with one of embodiments iii) to viii) above wherein V represents N, U represents N and W represents CH.

xiv) According to one main variant of this invention, the compounds of formula I as defined in one of embodiments i) to xiii) above will be such that A represents O.

xv) One sub-embodiment of embodiment xiv) relates to the compounds of formula I as defined in embodiment i) wherein:
A represents O;
$R^1$ represents methoxy;
U represents N and either V represents CH and W represents N or V represents N and W represents CH;
$R^2$ represents hydrogen;
Y represents CH;
Q represents O or S; and
n represents 1.

xvi) According to the other main variant of this invention, the compounds of formula I as defined in one of embodiments i) to xiii) above will be such that A represents $CH_2$.

xvii) One sub-embodiment of embodiment xvi) relates to the compounds of formula I as defined in embodiment i) wherein:
A represents $CH_2$;
$R^1$ represents methoxy;
U represents N and either V represents CH and W represents N or V represents N and W represents CH;
$R^2$ represents hydrogen;
Y represents CH;
Q represents O or S; and
n represents 1.

xviii) A particular embodiment of this invention relates to the compounds of formula I as defined in one of embodiments i) to xvii) above wherein $R^1$ represents $(C_1-C_3)$alkoxy (and in particular methoxy).

xix) Another particular embodiment of this invention relates to the compounds of formula I as defined in embodiment i) wherein:
$R^1$ represents methoxy;
U represents N and either V represents CH and W represents N or V represents N and W represents CH;
$R^2$ represents hydrogen;
A represents O or $CH_2$ (and preferably O);
Y represents CH;
Q represents O or S; and
n represents 1.

xx) Yet another particular embodiment of this invention relates to the compounds of formula I as defined in embodiment i) or as defined in embodiment i) taken in combination with one of embodiments iii) to xix) above wherein W represents CH or N and $R^2$ represents hydrogen.

xxi) Yet a further particular embodiment of this invention relates to the compounds of formula I as defined in embodiment i) or as defined in embodiment i) taken in combination with one of embodiments iii) to v), vii), ix), x), xiii), xiv), xvi) and xviii) above wherein W represents CH and $R^2$ represents fluorine.

xxii) According to another embodiment of this invention, the compounds of formula I as defined in one of embodiments i) to xxi) above will be such that n represents 0.

xxiii) According to yet another embodiment of this invention, the compounds of formula I as defined in one of embodiments i) to xxi) above will be such that n represents 1.

xxiv) Another embodiment of this invention relates to compounds of formula I as defined in one of embodiments i) to xxiii) as well as to isotopically labelled, especially $^2H$ (deuterium) labelled compounds of formula I as defined in one of embodiments i) to xxiii), which compounds are identical to the compounds of formula I as defined in one of embodiments i) to xxiii) except that one or more atoms has or have each been replaced by an atom having the same atomic number but an atomic mass different from the atomic mass usually found in nature. Isotopically labelled, especially $^2H$ (deuterium) labelled compounds of formula I and salts (in particular pharmaceutically acceptable salts) thereof are thus within the scope of the present invention. Substitution of hydrogen with the heavier isotope $^2H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

xxv) Particularly preferred are the following compounds of formula I as defined in embodiment i) or ii):
1-((S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-7-methoxy-1H-[1,8]naphthyridin-2-one;
1-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-7-methoxy-1H-[1,8]naphthyridin-2-one;
1-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-7-methoxy-1H-quinoxalin-2-one;

4-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-6-methoxy-4H-pyrido[2,3-b]pyrazin-3-one;

1-((2S)-2-{(2S,5R)-5-[(6,7-dihydro-[1,4]dioxino[2,3-c]pyridazin-3-ylmethyl)-amino]-tetrahydro-pyran-2-yl}-2-hydroxy-ethyl)-7-methoxy-1H-[1,8]naphthyridin-2-one;

1-((2R)-2-{4-[(2,3-dihydro-[1,4]dioxino[2,3-c]pyridin-7-ylmethyl)-amino]-cyclohexyl}-2-hydroxy-ethyl)-7-methoxy-1H-[1,8]naphthyridin-2-one;

1-((2R)-2-{4-[(2,3-dihydro-[1,4]dioxino[2,3-c]pyridin-7-ylmethyl)-amino]-cyclohexyl}-2-hydroxy-ethyl)-7-methoxy-1H-quinoxalin-2-one;

1-((2S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-7-methoxy-1H-[1,8]naphthyridin-2-one;

as well as the salts (in particular the pharmaceutically acceptable salts) thereof xxvi) The following compounds of formula I as defined in embodiment i) are also particularly preferred:

1-((2S)-2-hydroxy-2-{(2S,5R)-5-[(3-oxa-1-thia-5-aza-indan-6-ylmethyl)-amino]-tetrahydro-pyran-2-yl}-ethyl)-7-methoxy-1H-[1,8]naphthyridin-2-one;

3-fluoro-1-((2S)-2-hydroxy-2-{(2S,5R)-5-[(3-oxa-1-thia-5-aza-indan-6-ylmethyl)-amino]-tetrahydro-pyran-2-yl}-ethyl)-7-methoxy-1H-[1,8]naphthyridin-2-one;

4-((2S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-6-methoxy-4H-pyrido[2,3-b]pyrazin-3-one;

4-((2S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-6-methoxy-4H-pyrido[2,3-b]pyrazin-3-one;

5-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-3-methoxy-5H-pyrido[2,3-b]pyrazin-6-one;

5-((2S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-3-methoxy-5H-pyrido[2,3-b]pyrazin-6-one;

5-((S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-3-methoxy-5H-pyrido[2,3-b]pyrazin-6-one;

as well as the salts (in particular the pharmaceutically acceptable salts) thereof xxvii) The invention further relates to the compounds of formula I as defined in embodiment i) which are selected from the group consisting of the compounds listed in embodiment xxv) and the compounds listed in embodiment xxvi). In particular, it also relates to the groups of compounds of formula I selected from the group consisting of the compounds listed in embodiment xxv) and the compounds listed in embodiment xxvi), which groups of compounds furthermore correspond to one of embodiments iii) to xxiii), as well as to the salts (in particular the pharmaceutically acceptable salts) of such compounds. The invention moreover relates to any individual compound of formula I selected from the group consisting of the compounds listed in embodiment xxv) and the compounds listed in embodiment xxvi), and to the salts (in particular the pharmaceutically acceptable salts) of such individual compound.

The compounds of formula I according to the invention, i.e. according to one of embodiments i) to xxvii) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus* haemolyticum; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae, Streptococcal* groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; infections caused by *Mycobacterium tuberculosis, M leprae*, M paratuberculosis, *M. kansasii*, or M chelonei; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter* pylori or *Chlamydia pneumoniae*.

The compounds of formula I according to the present invention are further useful for the preparation of a medicament for the treatment of infections that are mediated by bacteria such as *E. coli, Klebsiella pneumoniae* and other *Enterobacteriaceae, Acinetobacter* spp. including *Acinetobacter baumanii, Stenothrophomonas maltophilia, Neisseria meningitidis, Bacillus cereus, Bacillus anthracis, Clostridium difficile, Corynebacterium* spp., *Propionibacterium acnes* and *bacteroide* spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of formula I according to this invention, or the pharmaceutically acceptable salt thereof, may be used for the preparation of a medicament, and are suitable, for the prevention or treatment of a bacterial infection.

One aspect of this invention therefore relates to the use of a compound of formula I according to one of embodiments i) to xxvii), or of a pharmaceutically acceptable salt thereof, for the manufacture of a medicament for the prevention or treatment of a bacterial infection. Another aspect of this invention relates to a compound of formula I according to one of embodiments i) to xxvii), or of a pharmaceutically acceptable salt thereof, for the prevention or treatment of a bacterial infection.

Accordingly, the compounds of formula I according to one of embodiments i) to xxvii), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium* difficile infections, urinary tract infections, sexually transmitted infections, foreign body infections, osteomyelitis, lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound of formula I according to one of embodiments i) to xxvii) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

The compounds of formula I can be manufactured in accordance with the present invention using the procedures described hereafter.

Preparation of the Compounds of Formula I

Abbreviations:

The following abbreviations are used throughout the specification and the examples:

| | |
|---|---|
| Ac | acetyl |
| AD-mix α | 1,4-bis(dihydroquinine)phthalazine, $K_3Fe(CN)_6$, $K_2CO_3$ and $K_2OsO_4·2H_2O$ |
| AD-mix β | 1,4-bis(dihydroquinidine)phthalazine, $K_3Fe(CN)_6$, $K_2CO_3$ and $K_2OsO_4·2H_2O$ |
| Alloc | allyloxycarbonyl |
| aq. | aqueous |
| Boc | tert-butoxycarbonyl |
| Bs | 4-bromobenzenesulfonyl (brosylate) |
| Cbz | benzyloxycarbonyl |
| CC | column chromatography over silica gel |
| DAD | diode array detection |
| DBU | 1,8-diazabicyclo[5.4.0]undec-7-ene |
| DCE | 1,2-dichloroethane |
| DCM | dichloromethane |
| (DHQ)$_2$PHAL | 1,4-bis(dihydroquinine)phthalazine |
| (DHQD)$_2$Pyr | 1,4-bis(dihydroquinidine)pyridine |
| DIBAH | diisobutylaluminium hydride |
| DIPEA | N,N-diisopropylethylamine |
| DMAP | 4-dimethylaminopyridine |
| DMF | N,N-dimethylformamide |
| DMSO | dimethylsulfoxide |
| EA | ethyl acetate |
| ELSD | Evaporative Light Scattering Detector |
| ESI | Electron Spray Ionisation |
| eq. | equivalent |
| Et | ethyl |
| ether | diethyl ether |
| EtOH | ethanol |
| Fmoc | 9-fluorenylmethoxycarbonyl |
| Hept | heptane |
| Hex | hexane |
| HPLC | high pressure liquid chromatography |
| LC | liquid chromatography |
| MCPBA | meta-chloroperbenzoic acid |
| Me | methyl |
| MeOH | methanol |
| MS | Mass Spectroscopy |
| Ms | methanesulfonyl (mesyl) |
| NCS | N-chlorosuccinimide |
| Nf | nonafluorobutanesulfonyl |
| Ns | 4-nitrobenzenesulfonyl (nosylate) |
| NMO | N-methyl-morpholine N-oxide |
| org. | organic |
| Pd/C | palladium on carbon |
| Pd(OH)$_2$/C | palladium dihydroxide on carbon |

| | |
|---|---|
| PTT | phenyltrimethylammonium tribromide |
| Pyr | pyridine |
| rac | racemic |
| rt | room temperature |
| sat. | saturated |
| tBu | tert-butyl |
| TEA | triethylamine |
| Tf | trifluoromethanesulfonyl (triflyl) |
| TBME | tert-butyl methyl ether |
| TFA | trifluoroacetic acid |
| THF | tetrahydrofuran |
| TLC | thin layer chromatography |
| TMSCl | trimethylsilyl chloride |
| Ts | para-toluenesulfonyl |
| wt % | percent in weight |

General Reaction Techniques:

General Reaction Technique 1 (Reduction of Aldehydes or Ketones into their Corresponding Alcohols):

The aldehydes or ketones can be reduced to the corresponding alcohols using a variety of reducing agents as reviewed by Larock, R. C. in *Comprehensive Organic Transformations A guide to Functional Group Preparations*, 2$^{nd}$ Ed., Wiley, New York, Chichester, Weinheim, Brisbane, Singapore, Toronto (1999), Section Alcohols and phenols; p. 1075 to 1110. Among them LiAlH$_4$ and NaBH$_4$ are the most preferred.

General Reaction Technique 2 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. NaBH$_4$, NaBHCN$_3$, or NaBH(OAc)$_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

General Reaction Technique 3 (Activation of an Alcohol):

The alcohol is reacted with MsCl, TfCl, NfCl, NsCl, BsCl or TsCl in presence of an org. base such as TEA, DIPEA or Pyr in a dry aprotic solvent such as DCM, THF or Pyr between −10° C. and rt. Alternatively, the alcohol can also be reacted with Ms$_2$O or Tf$_2$O. The activated intermediate can be further transformed into its corresponding iodo or bromo derivative by reaction of the activated alcohol with NaI or NaBr in a solvent such as acetone.

General Reaction Technique 4 (Removal of Amino Protecting Groups.):

The benzyl carbamates are deprotected by hydrogenolysis over a noble metal catalyst (e.g. Pd/C or Pd(OH)$_2$/C). The Boc group is removed under acidic conditions such as HCl in an organic solvent such as MeOH or dioxane, or TFA neat or diluted in a solvent such as DCM. Further general methods to remove amine protecting groups have been described in T. W. Greene, P. G. M. Wuts, *Protecting Groups in Organic Synthesis*, 3$^{rd}$ Ed (1999), 494-653 (Publisher: John Wiley and Sons, Inc., New York, N.Y.).

General Reaction Technique 5 (Amine Protection):

Amines are usually protected as carbamates such as Alloc, Cbz, Boc or Fmoc. They are obtained by reacting the amine with allyl or benzyl chloroformate, di tert-butyl dicarbonate or FmocCl in presence of a base such as NaOH, TEA, DMAP or imidazole. They can also be protected as N-benzyl derivatives by reaction with benzyl bromide or chloride in presence of a base such as Na$_2$CO$_3$ or TEA. Alternatively, N-benzyl derivatives can be obtained through reductive amination in presence of benzaldehyde and a borohydride reagent such as NaBH$_4$, NaBH$_3$CN or NaBH(OAc)$_3$ in a solvent such as MeOH, DCE or THF. Further strategies to introduce other amine protecting groups have been described in T. W. Greene, P. G. M. Wuts, *Protecting Groups in Organic Synthesis*, 3rd Ed (1999), 494-653 (Publisher: John Wiley and Sons, Inc., New York, N.Y.).

General Reaction Technique 6 (Formation of Aldehydes and Ketones):

The alcohols can be transformed into their corresponding aldehydes or ketones through oxidation under Swern (see D. Swern et al., *J. Org. Chem.* (1978), 43, 2480-2482) or Dess Martin (see D. B. Dess and J. C. Martin, *J. Org. Chem.* (1983), 48, 4155) conditions respectively. Alternatively, aldehydes can also be obtained from the corresponding esters by controlled reduction with a bulky hydride reagent such as DIBAH.

General Reaction Technique 7 (Asymmetric Dihydroxylation):

The chiral diols are obtained by using AD-mix α or AD-mix β in a water/2-methyl-2 propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Reaction Technique 8 (Asymmetric Reduction):

Chiral alcohols can be obtained from the corresponding prochiral ketones using a chiral reducing reagent. Boron-based reagents such as (R)- or (S)-tetrahydro-1-methyl-3,3-diphenyl-1H,3H-pyrrolo[1,2-c][1,3,2]oxaborole in the presence of a borane-tetrahydrofuran complex (see *J. Am. Chem. Soc.* (1987), 109, 5551), or B-chlorodiisopinocampheylborane (see *J. Org. Chem.* (1989), 54, 1577) are commonly used. Alternatively, chiral aluminium-based reagents can also be used. Such reagent combined an aluminium salt with a chiral promoter such as (R)- or (S)-2,2'-dihydroxy-1,1'-binaphthyl (see *J. Am. Chem. Soc.* (1984), 106, 6709). Catalytic asymmetric hydrogenation of prochiral ketones is also a widely used method for the obtention of chiral alcohols. For example, chiral ruthenium catalysts are useful catalysts for this purpose (see *Acc. Chem. Res.* (1997), 30, 97).

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) and b) hereafter describe general methods for preparing compounds of formula I. If not indicated otherwise, the generic groups R$^1$, U, W, A, Y and Q are as defined for formula I. General synthetic methods used repeatedly throughout the text below are referenced to and described in the above section entitled "General synthetic methods". Other abbreviations used are defined in the experimental section. In some instances the generic groups U, W, A and Y might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

a) The compounds of formula I can be obtained by reacting the compounds of formula II

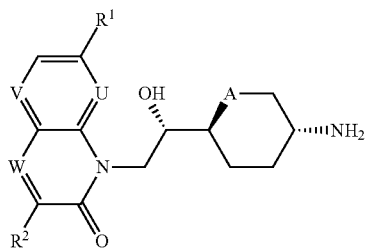

II with the compounds of formula III

G—CHO   III wherein G represents the group

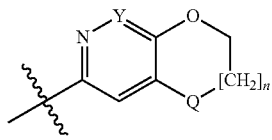

using general reaction technique 2.

b) The compounds of formula I can be obtained by reducing the compounds of formula IV

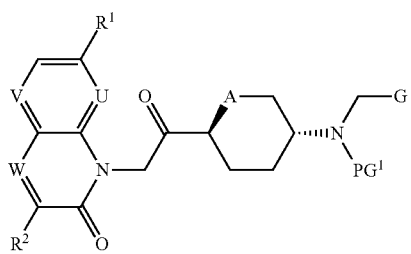

IV wherein $PG^1$ represents an amino protecting group such as Cbz, Fmoc or Boc and G represents the group

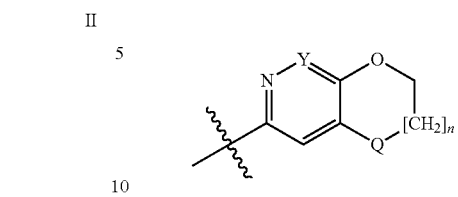

using a method described in general reaction technique 8 followed by removal of the amino protecting group according to general reaction technique 4. In the cases wherein A is O, general reaction technique 1 can also be used.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min. Whenever the compounds of formula I are obtained in the form of mixtures of diastereomers they may be separated by an appropriate combination of silica gel chromatography, HPLC and crystallization techniques.

Preparation of the Synthesis Intermediates:

The compounds of formula II can be prepared as described in Scheme 1 hereafter.

Scheme 1

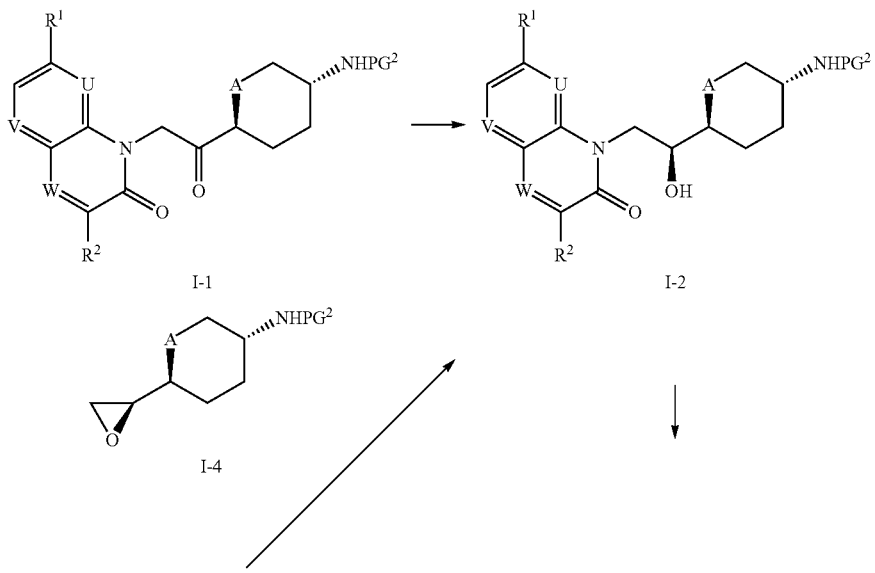

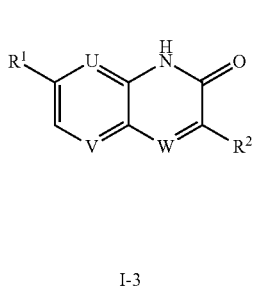

I-3

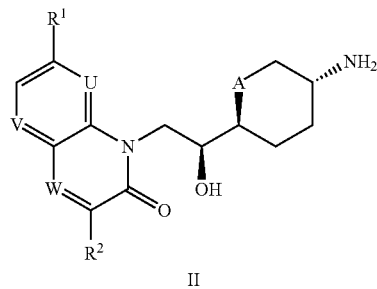

II

In Scheme 1, $PG^2$ represents an amino protecting group such as Cbz, Fmoc or Boc.

In the cases wherein A is O, the chiral ketone derivatives of formula I-1 can be diastereoselectively reduced using general reaction technique 1 or using general reaction technique 8. In the cases wherein A is $CH_2$, the chiral alcohol derivatives of formula I-1 can be obtained using general reaction technique 8. Alternatively, the alcohols of formula I-2 can also be obtained by reaction of the derivatives of formula I-3 with the epoxides of formula I-4 in presence of an inorganic base such as $Cs_2CO_3$. The compounds of formula II can then be obtained after removal of the amino protecting group following general reaction technique 4.

The aldehydes of formula III can be prepared according to WO 2006/002047, WO 2008/009700, WO 2008/128942 and WO 2007/138974.

The compounds of formulae I-1 and IV can be prepared as described in Scheme 2 hereafter.

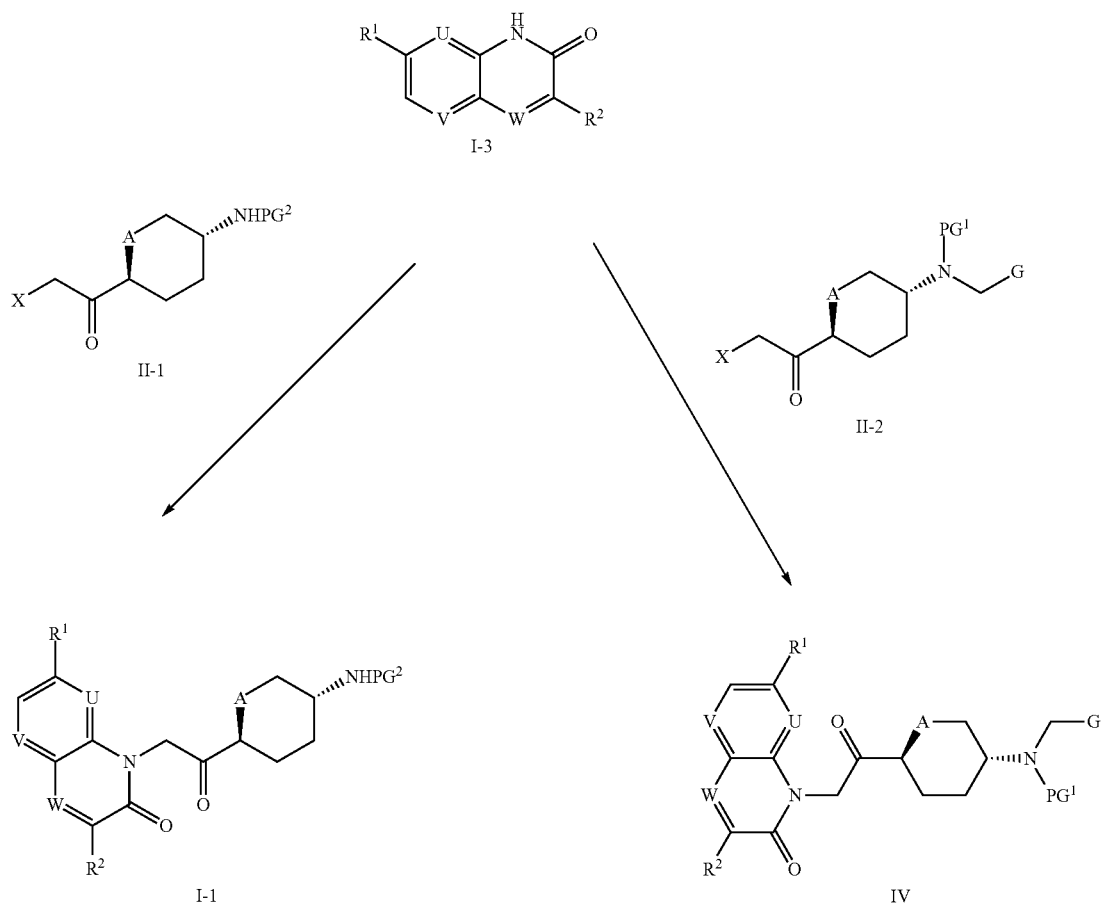

Scheme 2

In Scheme 2, X represents a halogen such as bromine, PG[1] and G are as defined in formula IV and PG[2] represents an amino protecting group such as Boc, Cbz or Fmoc.

Accordingly, the intermediates of formula I-3 can be reacted with the halogenomethyl ketones of formulae II-1 and II-2 in the presence of a base such as $K_2CO_3$ in a solvent such as THF or DMF between 40° C. and 100° C. to yield respectively the compounds of formulae I-1 and IV.

Preparation of the Starting Compounds:

The compounds of formula I-3 wherein R[1] is MeO are either commercial (U=V=W=CH or U=V=N and W=CH) or can be prepared according to literature (U=CH, W=N: WO 2008/009700; U=N, W=CH: *J. Heterocyclic Chem.* (1986), 23(2), 501-504; U=V=N: WO 2006/134378). The compound of formula I-3 wherein R[1] is MeO, U is N, R[2] is F and V and W are each CH can be obtained as described in Scheme 2a hereafter.

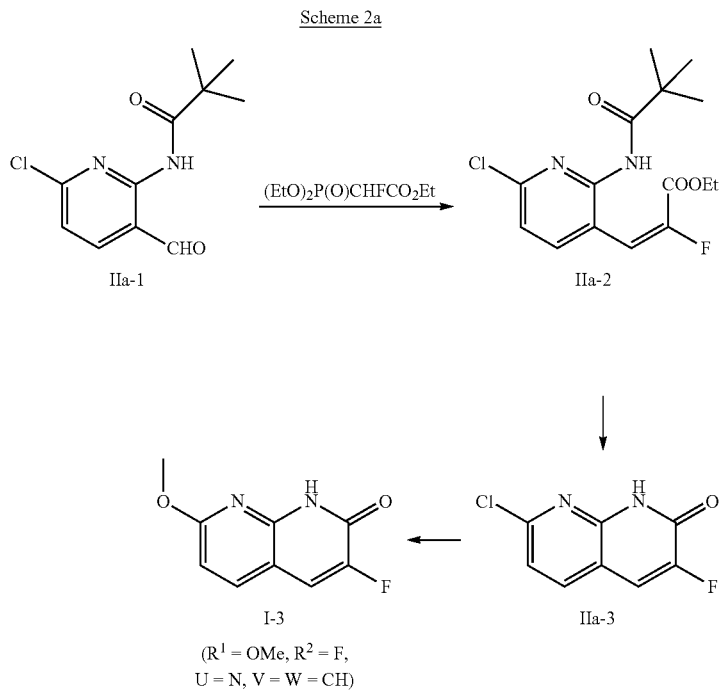

Scheme 2a

Thus, the 3-formyl pyridine derivative of formula IIa-1 (prepared according to *J. Org. Chem.* (1990), 55, 4744) can be reacted with triethyl 2-fluoro-phosphonoacetate. The resulting acrylate of formula IIa-2 can be cyclised under thermal conditions, affording the naphthridone derivative of formula IIa-3 which can be reacted with NaOMe to afford the compound of formula I-3 wherein R[1] is MeO, U is N, R[2] is F and V and W are each CH.

The compounds of formula I-4 can be prepared as described in Scheme 3 hereafter.

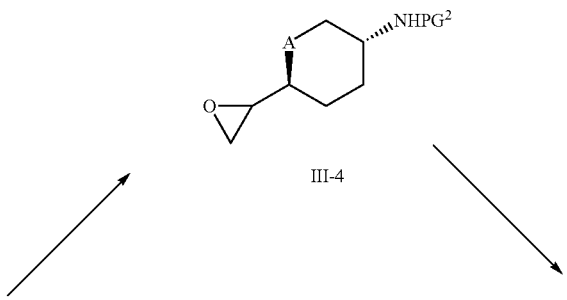

Scheme 3

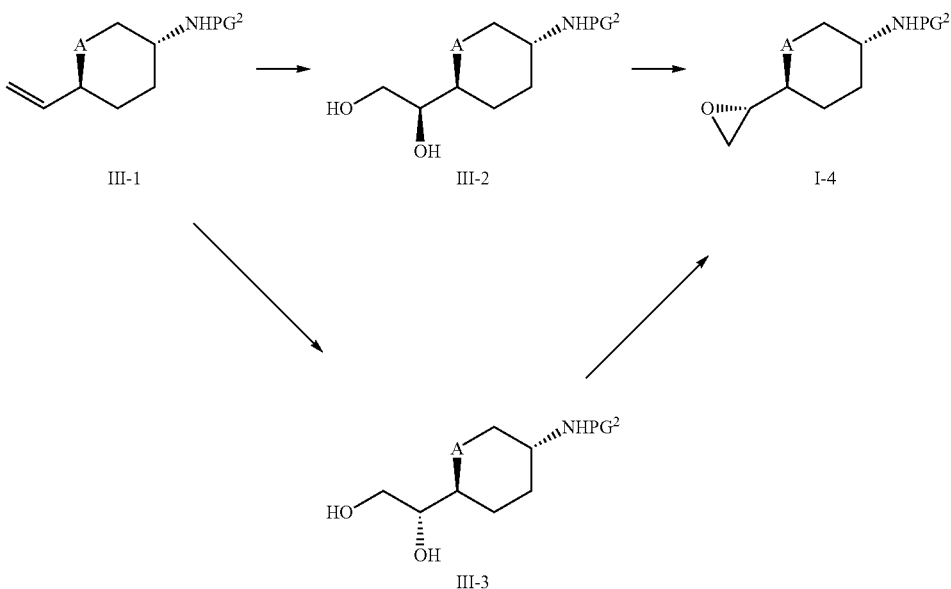

In Scheme 3, PG² represents an amino protecting group such as Boc, Cbz or Fmoc.

The ethylenic derivatives of formula III-1 (commercial e.g. when A=CH₂ and PG²=Boc or prepared according WO 2006/032466 e.g. when A=O and PG²=Boc) can be subjected to an achiral epoxidation using MCPBA or hydrogen peroxide in presence of a metal catalyst such as a vanadium (III) salt to give the epoxide of formula III-4. In the cases wherein A is CH₂, the chiral epoxides of formula I-4 can be obtained from the alkenes of formula III-1 via an asymmetric dihydroxylation using a dihydroquinidine-based chiral ligand (e.g. (DHDQ)₂Pyr) as described in general reaction technique 7. The resulting diols of formula III-2 can then be transformed into the corresponding epoxides of formula I-4 either after activation of the primary alcohol using general reaction technique 3 followed by epoxide formation in the presence of an alkali alkoxide such as sodium methoxide or through reaction with trimethylorthoacetate followed by reaction with TMSCl and epoxide formation in the presence of an alkali alcoholate (see *Tetrahedron* (1992), 48, 10515). In the cases wherein A is O, the chiral epoxides of formula I-4 are preferentially obtained through the chiral diols of formula III-3, stemming from the alkenes of formula III-1 via an asymmetric dihydroxylation using a quinidine-based chiral ligand (e.g. (DHQ)₂PHAL). The resulting diols of formula III-3 can then be transformed into the corresponding epoxides of formula I-4 via the protection of the primary alcohol as an ester (preferentially a pivalate ester obtained by treatment of the alcohol of formula III-3 with pivaloyl chloride in presence of an organic base such as TEA), the activation of the secondary alcohol using general reaction technique 3, and ring closure upon treatment with an alkali alcoholate such as sodium methoxide. Alternatively, the epoxides of formula I-4 can be obtained by hydrolytic kinetic resolution (HKR) catalyzed by chiral (salen)-Co(III) complex (e.g. [(R,R)—N,N'-bis(3,5-di-tert-butylsalicylidene)-1,2-cyclohexanediaminato(2-)]cobalt (III) complex) of the racemic epoxides as described by Jacobsen et al. in *J. Am. Chem. Soc.* (2002), 124, 1307-1315 and *Science* (1997), 277, 936-938. The chiral epoxides of formula I-4 can also be obtained through Shi chiral epoxidation the alkenes of formula III-1 using a chiral ketone as described in *Acc. Chem. Res.* (2004), 37, 488-496.

The compounds of formula II-1 wherein A is CH₂ and PG² is Boc or Cbz are commercially available. The other compounds of formula II-1 and the compounds of formula II-2 can be prepared for example as described in Scheme 4 hereafter.

Scheme 4

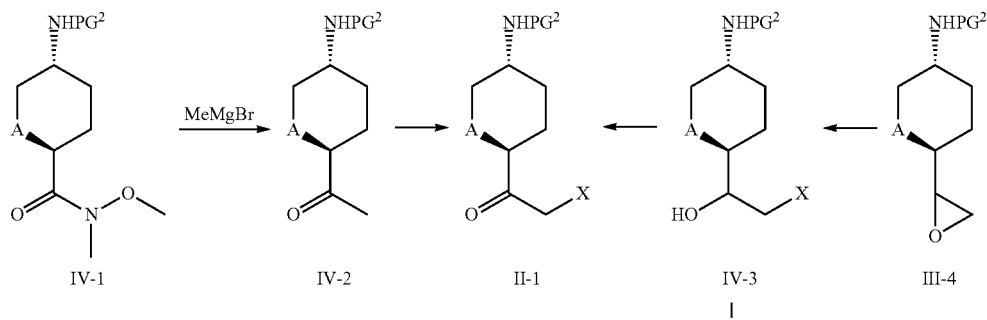

-continued

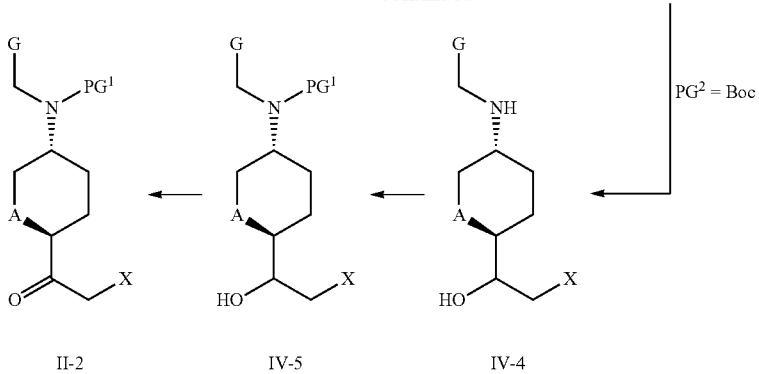

II-2     IV-5     IV-4

In Scheme 4, X represents a halogen such as bromine, PG$^1$ and PG$^2$ represent independently from each other amino protecting groups such as Cbz, Fmoc or Boc.

The compounds of formula II-1 can be obtained by reaction of the hydroxamate derivatives of formula IV-1 (commercially available when A=CH$_2$ or prepared from 5-(tert-butoxycarbonylamino)tetrahydropyran-2-carboxylic acid (see WO 2006/032466) and N,O-dimethyl hydroxylamine in presence of propanephosphonic acid anhydride and an organic base such as DIPEA) with methylmagnesium bromide. The ketones of formula IV-2 can be reacted with LiHDMS and PTT or NCS, affording the halogenomethylketone derivatives of formula II-1. These derivatives can also be obtained by opening the epoxides of formula III-4 with LiX (such as LiBr) or HX (such as HCl) followed by oxidation of the corresponding alcohol derivatives of formula IV-3 using general reaction technique 6. The compounds of formula II-2 can be obtained by removal of the protecting group of compounds of formula IV-3 followed by reductive amination with compounds of formula G-CHO using general reaction technique 2. The intermediates of formula IV-4 can be protected using general reaction technique 5, affording the intermediates of formula IV-5, which can then be oxidized into the compounds of formula II-2 using general reaction technique 6.

Particular embodiments of the invention are described in the following Examples, which serve to illustrate the invention in more detail without limiting its scope in any way.

EXAMPLES

All temperatures are stated in ° C. Compounds are characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad, coupling constants are given in Hz. Alternatively compounds are characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 F$_{254}$); or by melting point. Compounds are purified by chromatography on Silica gel 60A. NH$_4$OH as used for CC is 25% aq.

Preparation A: (3R,6S)-[6-((2S)-oxiranyl)-tetrahydro-pyran-3-yl]-carbamic acid tert-butyl ester A.i. (3R,6S)-(6-formyl-tetrahydro-pyran-3-yl)-carbamic acid tert-butyl ester To a solution of (3R,6S)-(6-hydroxymethyl-tetrahydro-pyran-3-yl)-carbamic acid tert-butyl ester (37.5 g, 162.13 mmol) in DCM (310 mL) cooled to −10° C. was added DIPEA (84.75 mL, 495.06 mmol). Then a solution of Pyr.SO$_3$ complex (50%, 69.47 g, 218.25 mmol) in DMSO (225 mL) was slowly added. The reaction mixture was stirred for 2 h at 0° C. The reaction mixture was partitioned between water (150 mL) and DCM (220 mL). The two layers were separated and the aq. layer was extracted twice with DCM (2×150 mL). The combined org. layers were dried over Na$_2$SO$_4$, filtered and concentrated to dryness. The residue was co-evaporated 3 times with toluene and purified over a short pad of silica gel (EA-Hept. 2-1) to afford the title aldehyde as a white solid (33.58 g, 90% yield).

MS (ESI, m/z): 230.0 [M+H$^+$] or C$_{11}$H$_{19}$NO$_4$.

A.ii. (3R,6S)-(6-vinyl-tetrahydro-pyran-3-yl)-carbamic acid tert-butyl ester tBuOK (31.74 g, 282.89 mmol) was added in one portion to a white suspension of methyl triphenylphosphonium bromide (101.05 g, 282.89 mmol) in THF (340 mL) at rt under nitrogen. The resulting orange suspension was stirred for 1 h at rt and a solution of intermediate A.i (32.43 g, 141.44 mmol) in THF (85 mL) was added. The mixture was stirred 30 minutes at rt. 10% aq. NaHSO$_4$ (120 mL) was added and the mixture was diluted with EA (200 mL). The two layers were decanted and the aq. layer was extracted once with EA (250 mL). The combined org. layers were washed with brine, dried over Na$_2$SO$_4$, filtered and concentrated to dryness. The residue was quickly filtered (EA-Hept 1-2 to EA-Hept 4-1) to afford the title compound as a white solid (28.98 g, 90% yield).

$^1$HNMR (CDCl$_3$) δ: 5.84 (ddd, J=5.6, 10.5, 17.3 Hz, 1H); 5.24 (dt, J=1.5, 17.3 Hz, 1H); 5.12 (dt, J=1.5, 10.5 Hz, 1H); 4.26 (br. s, 1H); 4.10 (ddd, J=2.1, 4.7, 10.8 Hz, 1H); 3.73 (m, 1H); 3.61 (m, 1H); 3.06 (t, J=10.5 Hz, 1H); 2.10 (m, 1H); 1.79 (m, 1H); 1.25-1.60 (m, 2H); 1.44 (s, 9H).

MS (ESI, m/z): 228.2 [M+H$^+$] for C$_{12}$H$_{21}$NO$_3$.

A.iii. (3R,6S)-{6-[(2R)-1,2-dihydroxy-ethyl]-tetrahydro-pyran-3-yl}-carbamic acid tert-butyl ester To a mixture of intermediate A.ii (29.98 g, 131.9 mmol) in 2-methyl-2-propanol (575 mL), EA (92 mL) and water (670 mL) were added K$_3$Fe(CN)$_6$ (130.28 g, 395.68 mmol, 3 eq.), K$_2$CO$_3$ (54.68 g, 395.68 mmol, 3 eq.), (DHQ)$_2$PHAL (0.72 g, 0.92 mmol, 0.01 eq.) and K$_2$OsO$_2$(OH)$_2$ (0.13 g, 0.36 mmol, 0.003 eq.). The mixture was stirred overnight at 0° C. NaHSO$_3$ (105 g) was added portion wise at 0° C. and the reaction proceeded for 15 min. The reaction mixture was extracted with water and EA. The org. layer was washed with brine, and dried over Na$_2$SO$_4$, then filtered and concentrated under reduced pressure. The residue was purified by CC (DCM-MeOH 97-3 to 9-1) to afford the title diol as a white solid (27.84 g, 81% yield). The compound was obtained as a 6-1 mixture of diastereomers.

$^1$H NMR (CDCl$_3$) major diastereomer δ: 4.23 (br. s, 1H); 4.09 (ddd, J=2.4, 5.1, 10.5 Hz, 1H); 3.68-3.74 (m, 2H); 3.52-3.66 (m, 2H); 3.35 (ddd, J=2.4, 5.1, 11.4 Hz, 1H); 2.98 (t, J=10.8 Hz, 1H); 2.51 (br. d, J=6.0 Hz, 1H); 2.09-2.21 (m, 2H); 1.78 (m, 1H); 1.54 (m, 1H); 1.43 (s, 9H); 1.22-1.36 (m, 1H).

MS (ESI, m/z): 262.4 [M+H$^+$] for C$_{12}$H$_{23}$NO$_5$.

A.iv. 2,2-dimethyl-propionic acid (2R)-2-[(2S,5R)-(5-tert-butoxycarbonylamino-tetrahydro-pyran-2-yl]-2-hydroxy-ethyl ester To a solution of intermediate A.iii (27.84 g, 106.54 mmol) and DMAP (26.03 g, 213.08 mmol, 2 eq.) in DCM (510 mL), cooled to −15° C., was added trimethyl acetyl chloride (17.06 mL, 138.5 mmol, 1.3 eq.). The reaction proceeded 1 h. MeOH (28 mL) then sat. NaHCO$_3$ (250 mL) were added. The two layers were separated and the aq. layer was extracted with EA (200 mL). The combined org. layers were dried over Na$_2$SO$_4$, filtered and concentrated to dryness. After CC of the oily residue (Hept-EA 3-1 to 1-1), the title compound was obtained as a white solid (22.66 g, 62% yield).

MS (ESI, m/z): 346.1 [M+H$^+$] for C$_{17}$H$_{31}$NO$_6$.

Bis-pivalate (13.1 g, 29% yield) was also recovered and can be converted back to the intermediate A.iii in quantitative yield upon treatment with tBuOK in MeOH.

A.v. 2,2-dimethyl-propionic acid (2R)-2-[(2S,5R)-5-tert-butoxycarbonylamino-tetrahydro-pyran-2-yl]-2-methanesulfonyloxy-ethyl ester To a solution of intermediate A.iv (22.62 g, 65.48 mmol) in DCM (328 mL), cooled to 0° C. were added TEA (18.23 mL, 130.97 mmol, 2 eq.) and MsCl (5.58 mL, 72.03 mmol, 1.1 eq.). The reaction was stirred at 0° C. for 45 min. Sat. NaHCO$_3$ (250 mL) and DCM (200 mL) were added. The two layers were decanted and the org. layer was dried over Na$_2$SO$_4$, filtered and concentrated to dryness. The oil was filtered over a silica gel pad (5.5×10 cm, EA-Hept 1-1) to afford the title compound as a white foam (27.87 g, 100% yield).

MS (ESI, m/z): 424.3 [M+H$^+$] for C$_{18}$H$_{33}$NO$_8$S.

A.vi. (3R,6S)-[6-((2S)-oxiranyl)-tetrahydro-pyran-3-yl]-carbamic acid tert-butyl ester To a solution of intermediate A.v (27.85 g, 65.76 mmol) in THF (340 mL) was added NaOMe (in 25 wt % solution in MeOH, 30.1 mL, 2 eq.). The mixture was stirred at RT for 20 min. The reaction mixture was partitioned between 10% NaHSO$_4$ (220 mL) and EA (250 mL). The org. layer was dried over Na$_2$SO$_4$, filtered and concentrated under reduced pressure. The oil was purified by CC (EA-Hept 1-1) to afford the title epoxide as a white solid (10.78 g). The compound was obtained as a 6:1 mixture of diastereomers.

$^1$H NMR (CDCl$_3$) major diastereomer δ: 4.22 (br. s, 1H); 4.11 (m, 1H); 3.60 (br. s, 1H); 2.92-3.11 (m, 3H); 2.78 (m, 1H); 2.64 (m, 1H); 2.11 (m, 1H); 1.54-1.78 (m, 2H); 1.43 (s, 9H); 1.27 (qd, J=4.2, 12.3 Hz, 1H).

MS (ESI, m/z): 244.3 [M+H$^+$] for C$_{12}$H$_{21}$NO$_4$.

Preparation B:
7-methoxy-1H-[1,8]naphthyridin-2-one

To a solution of 7-chloro-1H-[1,8]naphthyridin-2-one (prepared as described in *J. Org. Chem.* (1990), 55, 4744; 5.36 g, 29.68 mmol) in MeOH (98 mL) was added NaOMe (25 wt % in MeOH, 161 mL). The resulting solution was stirred at reflux for 15 h. The solvent was removed in vacuo. Water (100 mL) and EA (80 mL) were added. The phases were separated and the aq. layer was extracted with EA (8×80 mL). The combined org. layers were washed with brine (50 mL), dried over MgSO$_4$, filtered and evaporated under reduced pressure. The title compound was obtained as a beige solid (5.22 g, 100% yield).

$^1$H NMR (d$_6$DMSO) δ: 11.96 (s, 1H); 7.96 (d, J=8.5 Hz, 1H); 7.81 (d, J=9.4 Hz, 1H); 6.63 (d, J=8.5 Hz, 1H); 6.34 (d, J=9.4 Hz, 1H); 3.90 (s, 3H).

Preparation C:
trans-(R)-(4-oxiranyl-cyclohexyl)-carbamic acid tert-butyl ester

C.i. Trans-(4-vinyl-cyclohexyl)-carbamic acid tert-butyl ester

Starting from trans-(4-hydroxymethyl-cyclohexyl)-carbamic acid tert-butyl ester (22 g, 95.9 mmol), the title alkene was obtained as a white solid (13.58 g) using the procedure of Preparation A, steps A.i and A.ii.

$^1$H NMR (d$_6$DMSO) δ: 6.65 (m, 1H); 5.73 (ddd, J=6.4, 10.2, 16.6 Hz, 1H); 4.95 (ddd, J=1.9, 2.1, 16.6 Hz, 1H); 4.86 (ddd, J=1.2, 2.1, 10.2 Hz, 1H); 3.12 (m, 1H); 1.62-1.89 (m, 5H); 1.35 (s, 9H), 1.00-1.28 (m, 4H).

MS (ESI, m/z): 226.2 [M+H$^+$] for C$_{13}$H$_{23}$NO$_2$.

C.ii. Trans-[4-(2R)-1,2-dihydroxy-ethyl)-cyclohexyl]-carbamic acid tert-butyl ester To a mixture of intermediate C.i (21.65 g, 96.08 mmol) in 2-methyl-2-propanol (480 mL) and water (480 mL) were added K$_3$Fe(CN)$_6$ (94.9 g), K$_2$CO$_3$ (39.9 g), (DHQD)$_2$Pyr (0.847 g) and K$_2$OsO$_2$(OH)$_2$ (0.354 g). The mixture was stirred at 0° C. for 30 h. The reaction was then carefully quenched with NaHSO$_3$ (112 g). The two layers were then decanted and the aq. layer was extracted once with EA (400 mL). The combined org. layers were dried over Na$_2$SO$_4$, filtered and concentrated to dryness. The residue was purified by CC (DCM-MeOH 9-1) to afford the title compound as a yellow solid (23.02 g, 92% yield).

$^1$H NMR (d$_6$DMSO) δ: 6.61 (m, 1H); 4.32 (t, J=5.6 Hz, 1H); 4.24 (d, J=5.0 Hz, 1H); 3.21-3.36 (m, 2H); 3.15 (m, 1H); 3.074 (m, 1H); 1.66-1.80 (m, 4H); 1.53 (m, 1H); 1.35 (s, 9H), 1.00-1.26 (m, 4H).

C.iii. Trans-(R)-(4-oxiranyl-cyclohexyl)-carbamic acid tert-butyl ester

To a solution of intermediate C.ii (23.02 g, 88.762 mmol) in DCM (240 mL) was added TsOH (0.795 g, 0.05 eq.) and trimethyl orthoacetate (16.1 mL, 1.3 eq.). The reaction proceeded at rt for 30 min. The solvents were removed under reduced pressure. The residue was taken up in DCM (120 mL) and MeOH (0.03 mL). TMS-Cl (16.0 mL, 1.4 eq.) was added. The reaction was stirred at rt for 1 h. Sat. NaHCO$_3$ (250 mL) was added and the two layers were separated. The org. layer was dried over Na$_2$SO$_4$, filtered and concentrated to dryness. The residue was taken up in MeOH (150 mL) and NaOMe (25% wt in MeOH, 40.5 mL) was added. The reaction proceeded at rt for 1 h. The reaction mixture was diluted with DCM (300 mL) and aq. NaHSO$_4$ (10%, 120 mL). The aq. layer was extracted three times with DCM-MeOH 9-1 (3×150 mL). The combined org. layers were washed with brine (200 mL), dried over Na$_2$SO$_4$, filtered and concentrated to give a yellow oil. After CC of the residue (EA:Hept 2:1), the title compound was obtained as a white solid (17.35 g, 81% yield).

$^1$H NMR (CDCl$_3$) δ: 4.37 (br. s, 1H); 3.39 (br. s, 1H); 2.68-2.75 (m, 2H); 2.52 (m, 1H); 2.02-2.10 (m, 2H); 1.96 (m, 1H); 1.75 (m, 1H); 1.45 (s, 9H); 1.00-1.36 (m, 5H).

Example 1

1-((S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-7-methoxy-1H-[1,8]naphthyridin-2-one

1.i. {(3R,6S)-6-[(1S)-1-hydroxy-2-(7-methoxy-2-oxo-2H[1,8]-naphthyridin-1-yl)-ethyl]-tetrahydro-pyran-3-yl}-carbamic acid tert-butyl ester To a solution of the compound of Preparation B (2.65 g, 15 mmol) and the compound of Preparation A (3.65 g, 15 mmol) in DMF (24 mL) was added Cs$_2$CO$_3$ (5.23 g, 16.05 mmol). The mixture was heated to 80° C. for 7 h. The solvent was removed under reduced pressure and the residue was partitioned between water (100 mL) and EA (100 mL). The aq. layer was extracted once more with EA (100 mL). The combined org. layers were dried over Na$_2$SO$_4$, filtered and evaporated under reduced pressure. The residue was purified by CC (Hept-EA 1-4 to 0-1) to afford the title compound as a white solid (3.50 g, 56% yield).

$^1$H NMR (d$_6$DMSO) δ: 8.01 (d, J=8.5 Hz, 1H); 7.82 (d, J=9.4 Hz, 1H); 6.69 (d, J=8.5 Hz, 1H); 6.69 (overlapped m, 1H); 6.47 (d, J=9.4 Hz, 1H); 4.65 (dd, J=8.8, 12.6 Hz, 1H); 4.43 (d, J=7.0 Hz, 1H); 4.32 (dd, J=4.1, 12.6 Hz, 1H); 3.96 (s, 3H); 3.91 (overlapped m 1H); 3.80 (m, 1H); 3.30 (m, 1H); 3.13 (m, 1H); 2.90 (t, J=10.5 Hz, 1H); 1.86 (m, 1H); 1.53-1.63 (m, 2H), 1.34 (s, 9H); 1.33 (overlapped m, 1H).

MS (ESI, m/z): 420.3 [M+H$^+$] for C$_{21}$H$_{29}$N$_3$O$_6$.

1.ii. 1-[(2S)-2-(2S,5R)-5-amino-tetrahydro-pyran-2-yl)-2-hydroxy-ethyl]-7-methoxy-1H-[1,8]-naphthyridin-2-one A solution of intermediate 1.i. (3.5 g, 8.34 mmol) in TFA (11 mL) and DCM (5 mL) was stirred at rt for 20 min. The volatiles were removed in vacuo and the residue was partitioned between sat. NaHCO$_3$ (20 mL) and DCM-MeOH (9-1, 100 mL) and the pH of the aq. layer was adjusted to 11 adding a concentrated NaOH solution. The aq. layer was extracted six times with DCM-MeOH mixture (9-1, 6×75 mL). The combined org. extracts were washed with brine (50 mL), dried over Na$_2$SO$_4$, filtered and concentrated to dryness to afford the title compound as an off-white foam (2.0 g, 75% yield).

$^1$H NMR (d6DMSO) δ: 8.01 (d, J=8.5 Hz, 1H); 7.82 (d, J=9.4 Hz, 1H); 6.69 (d, J=8.5 Hz, 1H); 6.47 (d, J=9.4 Hz, 1H); 4.65 (dd, J=8.8, 12.9 Hz, 1H); 4.30-4.37 (m, 2H); 3.94 (s, 3H); 3.92 (m, 1H); 3.76 (m, 1H); 3.12 (m, 1H); 2.79 (t, J=10.3 Hz, 1H); 2.53 (m, 1H); 1.89 (m, 1H); 1.50-1.59 (m, 2H); 1.30 (br. s, 2H); 1.13 (m, 1H).

MS (ESI, m/z): 320.3 [M+H$^+$] for C$_{16}$H$_{21}$N$_3$O$_4$.

1. iii. 1-((S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-7-methoxy-1H-[1,8]-naphthyridin-2-one To a solution of intermediate 1.ii (0.112 g, 0.353 mmol) in DCE (4.5 mL) and MeOH (1.5 mL) were added 3 Å molecular sieves (1.1 g) and 2,3-dihydro-4-oxa-1-thia-6-aza-naphthalene-7-carbaldehyde (0.064 g, 0.357 mmol). The mixture was stirred overnight at 50° C. After cooling, NaBH$_4$ (0.11 g) was added. The reaction proceeded for 45 min. The reaction mixture was diluted in DCM-MeOH (9-1, 100 mL). The solids were filtered off, washed with DCM (50 mL). The filtrate was washed with sat. NaHCO$_3$ (50 mL), dried over Na$_2$SO$_4$, filtered and concentrated to dryness. The residue was purified by CC (DCM-MeOH 9:1 containing 1% aq. NH$_4$OH) affording the title compound as a white foam (0.051 g, 30% yield).

$^1$H NMR (d6DMSO) δ: 8.01 (d, J=8.5 Hz, 1H); 7.95 (s, 1H); 7.82 (d, J=9.4 Hz, 1H); 7.13 (s, 1H); 6.68 (d, J=8.5 Hz, 1H); 6.46 (d, J=9.4 Hz, 1 H); 4.64 (dd, J=8.8, 12.9 Hz, 1H); 4.28-4.38 (m, 4H); 3.87-3.96 (m, 2H); 3.93 (s, 3H); 3.64 (AB syst., J=14.4 Hz, Δ=0.059 ppm, 2H); 3.21-3.26 (m, 2H); 3.17 (m, 1H); 2.88 (t, J=10.3 Hz, 1H); 2.43 (m, 1H); 1.94-2.07 (m, 2H); 1.42-1.62 (m, 2H); 1.18 (m, 1H).

MS (ESI, m/z): 485.2 [M+H$^+$] for C$_{24}$H$_{28}$N$_4$O$_5$S.

Example 2

1-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-7-methoxy-1H-[1,8]naphthyridin-2-one Starting from intermediate 1.ii (0.1 g, 0.31 mmol) and 2,3-dihydro-[1,4]dioxino[2,3-c]pyridine-7-carbaldehyde (0.052 g, 1.02 eq.), the title compound was obtained as a white foam (0.088 g, 61% yield) using the procedure of Example 1, step 1.iii. The crude material was purified by CC (DCM-MeOH 93:7 containing 0.7% aq. NH$_4$OH).

$^1$H NMR (d6DMSO) δ: 8.01 (d, J=8.5 Hz, 1H); 7.99 (s, 1H); 7.83 (d, J=9.4 Hz, 1H); 6.91 (s, 1H); 6.69 (d, J=8.5 Hz, 1H); 6.47 (d, J=9.4 Hz, 1 H); 4.65 (dd, J=8.8, 12.9 Hz, 1H); 4.38 (d, J=6.4 Hz, 1H); 4.24-435 (m, 5H); 3.86-3.96 (m, 2H); 3.94 (s, 3H); 3.61-3.71 (m, 2H); 3.17 (m, 1H); 2.89 (t, J=10.3 Hz, 1H); 2.43 (m, 1H); 1.93-2.09 (m, 2H); 1.45-1.62 (m, 2H); 1.19 (m, 1H).

MS (ESI, m/z): 469.2 [M+H$^+$] for C$_{24}$H$_{28}$N$_4$O$_6$.

Example 3

1-((2S)-2-{(2S,5R)-5-[(2,3-dihydro-[1,4]dioxino[2,3-c]pyridin-7-ylmethyl)-amino]tetrahydro-pyran-2-yl}-2-hydroxy-ethyl)-7-methoxy-1H-quinoxalin-2-one

3.i. 4-[(2S)-2-((2S,5R)-5-amino-tetrahydro-pyran-2-yl)-2-hydroxy-ethyl]-6-methoxy-4H-pyrido[2,3-b]-pyrazin-3-one Starting from the compound of Preparation A (1.43 g, 5.90 mmol) and 7-methoxy-1H-quinoxalin-2-one (1.04 g, 5.9 mmol), the title compound was obtained as a yellowish foam (0.168 g) using the procedures of Example 1, steps 1.i (epoxide opening, 45% yield) and 1.ii (Boc deprotection, 49% yield starting from 0.45 g of the intermediate). The crude reaction mixtures were purified by CC using an appropriate mixture of solvents.

MS (ESI, m/z): 320.3 [M+H$^+$] for C$_{16}$H$_{21}$N$_3$O$_4$.

3. ii. 1-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-7-methoxy-1H-quinoxalin-2-one Starting from intermediate 3.i (0.082 g, 0.257 mmol) and 2,3-dihydro-[1,4]dioxino[2,3-c]pyridine-7-carbaldehyde (0.043 g, 1.002 eq.) and using the procedure of Example 1, step 1.iii (reductive amination), the title compound was obtained as an off-white foam (0.045 g, 37% yield). The reaction mixture was purified by CC (DCM-MeOH 93-7 containing 0.7% aq. NH$_4$OH).

$^1$H NMR (d6DMSO) δ: 8.02 (s, 1H); 8.00 (s, 1H); 7.72 (d, J=8.8 Hz, 1H); 7.09 (d, J=2.6 Hz, 1H); 6.97 (dd, J=2.6, 8.8 Hz, 1H); 6.92 (s, 1H); 4.93 (d, J=6.4 Hz, 1H); 4.23-4.36 (m, 5H); 4.15 (dd, J=4.4, 12.6 Hz, 1H); 3.98 (m, 1H); 3.86 (s, 3H); 3.78 (m, 1H); 3.67 (AB syst., J=14.4 Hz, Δ=0.06 ppm, 2H); 3.21 (m, 1H); 2.92 (t, J=10.3 Hz, 1H); 2.46 (m, 1H); 2.13 (br. s, 1H); 2.00 (m, 1H); 1.46-1.63 (m, 2H); 1.19 (m, 1H).

MS (ESI, m/z): 469.0 [M+H$^+$] for C$_{24}$H$_{28}$N$_4$O$_6$.

Example 4

4-((2S)-2-{(2S,5R)-5-[(2,3-dihydro-[1,4]dioxino[2, 3-c]pyridin-7-ylmethyl)-amino]tetrahydro-pyran-2-yl}-2-hydroxy-ethyl)-6-methoxy-4H-pyrido[2,3-b] pyrazin-3-one 4.i. 4-[(2S)-2-((2S,5R)-5-Amino-tetrahydro-pyran-2-yl)-2-hydroxy-ethyl]-6-methoxy-4H-pyrido[2,3-b]-pyrazin-3-one Starting from 6-methoxy-4H-pyrido[2,3-b]pyrazin-3-one (0.425 g, 2.4 mmol) and the compound of Preparation A (0.584 g, 2.4 mmol), the title amine was obtained as a yellowish foam using the procedures of Example 1, steps 1.i (epoxide opening, 37% yield) and 1.ii (Boc deprotection, 100% yield). If necessary, the crude reaction mixtures were purified by CC using an appropriate mixture of solvents.

MS (ESI, m/z): 312.3 [M+H$^+$] for C$_{15}$H$_{20}$N$_4$O$_4$.

4.ii. 4-((2S)-2-{(2S,5R)-5-[(2,3-dihydro-[1,4]dioxino [2,3-c]pyridin-7-ylmethyl)-amino]-tetrahydro-pyran-2-yl}-2-hydroxy-ethyl)-6-methoxy-4H-pyrido[2,3-b] pyrazin-3-one Starting from intermediate 4.i (0.097 g, 0.304 mmol) and 2,3-dihydro-[1,4]dioxino[2,3-c]pyridine-7-carbaldehyde (0.055 g, 1.1 eq.), the title compound was obtained as a yellowish foam (0.027 g, 19% yield) using the procedure of Example 1, step 1.iii. The crude material was purified by CC (DCM-MeOH 93:7 containing 0.7% aq. NH$_4$OH).

$^1$H NMR (d6DMSO) δ: 8.09 (d, J=8.5 Hz, 1H); 8.07 (s, 1H); 7.98 (s, 1H); 6.91 (s, 1H); 6.79 (d, J=8.5 Hz, 1H); 4.60 (overlapped dd, J=8.8, 12.6 Hz, 1H); 4.59 (d, J=6.8 Hz, 1H); 4.30-4.34 (m, 2H); 4.24-4.28 (m, 2H); 4.20 (dd, J=3.8, 12.6 Hz, 1H); 3.87-3.99 (m, 2H); 3.94 (s, 3H); 3.65 (AB syst., J=14.4 Hz, Δ=0.06 ppm, 2H); 3.20 (m, 1H); 2.89 (t, J=10.5 Hz, 1H); 2.46 (m, 1H); 2.11 (br. s, 1H); 1.99 (m, 1H); 1.46-1.63 (m, 2H); 1.19 (m, 1H).

MS (ESI, m/z): 470.2 [M+H$^+$] for C$_{23}$H$_{26}$N$_6$O$_6$.

Example 5

1-((2S)-2-{(2S,5R)-5-[(6,7-dihydro-[1,4]dioxino[2, 3-c]pyridazin-3-ylmethyl)-amino]tetrahydro-pyran-2-yl}-2-hydroxy-ethyl)-7-methoxy-1H-[1,8]naphthyridin-2-one Starting from intermediate 1.ii (0.1 g, 0.31 mmol) and 6,7-dihydro-[1,4]dioxino[2,3-c]pyridazine-3-carbaldehyde (0.052 g, 1.02 eq.), the title compound was obtained as a white foam (0.039 g, 27% yield) using the procedure of Example 1, step 1.iii. The crude material was purified by CC (DCM-MeOH 93:7 containing 0.7% aq. NH$_4$OH).

$^1$H NMR (d6DMSO) δ: 8.01 (d, J=8.5 Hz, 1H); 7.83 (d, J=9.4 Hz, 1H); 7.17 (s, 1H); 6.69 (d, J=8.5 Hz, 1H); 6.47 (d, J=9.4 Hz, 1 H); 4.64 (dd, J=8.8, 12.6 Hz, 1H); 4.47-4.52 (m, 2H); 4.36-4.42 (m, 3H); 4.31 (dd, J=4.4, 12.6 Hz, 1H); 3.88-3.94 (m, 2H); 3.94 (s, 3H); 3.81-3.86 (m, 2H); 3.17 (m, 1H); 2.89 (t, J=10.3 Hz, 1H); 2.41 (m, 1H); 2.27 (m, 1H); 1.99 (m, 1H); 1.47-1.62 (m, 2H); 1.19 (m, 1H).

MS (ESI, m/z): 470.2 [M+H$^+$] for C$_{23}$H$_{27}$N$_5$O$_6$.

Example 6

1-((2R)-2-{4-[(2,3-dihydro-[1,4]dioxino[2,3-c]pyridin-7-ylmethyl)-amino]cyclohexyl}-2-hydroxy-ethyl)-7-methoxy-1H-[1,8]naphthyridin-2-one 6.i. 1-[(2R)-2-trans-(4-amino-cyclohexyl)-2-hydroxy-ethyl]-7-methoxy-1H-[1,8]-naphthyridin-2-one Starting from the compound of Preparation C (1.17 g, 4.82 mmol) and the compound of Preparation B (0.85 g, 4.82 mmol), the title compound was obtained as a white foam (0.494 g) using the procedures of Example 1, step 1.i (epoxide opening, 39% yield) and Example 1, step 1.ii (Boc deprotection, 84% yield). The crude reaction mixtures were purified by CC using an appropriate mixture of solvents.

$^1$H NMR (d6DMSO) δ: 8.01 (d, J=8.5 Hz, 1H); 7.82 (d, J=9.4 Hz, 1H); 6.69 (d, J=8.5 Hz, 1H); 6.47 (d, J=9.4 Hz, 1H); 4.55 (dd, J=8.8, 12.6 Hz, 1H); 4.33 (br. s, 1H); 4.28 (dd, J=4.1, 12.6 Hz, 1H); 3.94 (s. 3H); 3.78 (m, 1H); 3.26 (br. s, 2H); 2.42 (m, 1H); 1.88 (m, 1H), 1.81-1.71 (m, 2H); 1.62 (m, 1H); 1.08-1.30 (m, 3H); 0.85-1.02 (m, 2H).

MS (ESI, m/z): 318.2 [M+H$^+$] for C$_{17}$H$_{23}$N$_3$O$_3$.

6.ii. 1-((2R)-2-{4-[(2,3-dihydro-[-1,4]dioxino[2,3-c] pyridin-7-ylmethyl)-amino]-cyclohexyl}-2-hydroxy-ethyl)-7-methoxy-1H-[1,8]naphthyridin-2-one Starting from the intermediate 6.i (0.1 g, 0.315 mmol) and 2,3-dihydro-[1,4]dioxino[2,3-c]pyridine-7-carbaldehyde (0.053 g, 1.02 eq.), the title compound was obtained as a white foam (0.117 g, 80% yield) using the procedure of Example 1, step 1.iii. The crude material was purified by CC (DCM-MeOH 93:7 containing 0.7% aq. NH$_4$OH).

$^1$H NMR (d6DMSO) δ: 8.01 (d, J=8.5 Hz, 1H); 7.98 (s, 1H); 7.82 (d, J=9.4 Hz, 1H); 6.90 (s, 1H); 6.68 (d, J=8.5 Hz, 1H); 6.47 (d, J=9.4 Hz, 1H); 4.56 (dd, J=8.5, 12.3 Hz, 1H); 4.23-4.33 (m, 6H); 3.94 (s. 3H); 3.78 (m, 1H); 3.65 (s, 2H); 2.26 (m, 1H); 2.03 (br. s, 1H); 1.85-1.95 (m, 3H); 1.65 (m, 1H); 0.88-1.30 (m, 5H).

MS (ESI, m/z): 467.2 [M+H$^+$] for C$_{25}$H$_{30}$N$_4$O$_5$.

Example 7

1-((2R)-2-{4-[(2,3-dihydro-[1,4]dioxino[2,3-c]pyridin-7-ylmethyl)-amino]-cyclohexyl}-2-hydroxy-ethyl)-7-methoxy-1H-quinoxalin-2-one 7.i. Trans-{4-[(1R)-1-hydroxy-2-(7-methoxy-2-oxo-2H-quinoxalin-1-yl)-ethyl]-cyclohexyl}-carbamic acid tert-butyl ester To a solution of the compound of Preparation C (1.58 g, 6.55 mmol) in DMF (33 mL) was added 7-methoxy-1H-quinoxalin-2-one (1.18 g, 1.02 eq.) and Cs$_2$CO$_3$ (4.27 g, 2 eq.). The reaction mixture was stirred at 80° C. for 4 h. The solvent was removed under reduced pressure, and the residue was partitioned between water (50 mL) and EA (50 mL). The aq. layer was extracted once more with EA (50 mL). The org. layer was dried over $Na_2SO_4$, filtered and evaporated under reduced pressure. The residue was purified by CC (DCM-MeOH 99-1 then 95-5) to afford the title compound as a yellow solid (0.800 g, 29% yield).

MS (ESI, m/z): 418.1 [M+H$^+$] for $C_{22}H_{31}N_3O_5$.

7. ii. 1-[(2R)-2-trans-(4-amino-cyclohexyl)-2-hydroxy-ethyl]-7-methoxy-1H-quinoxalin-2-one Starting from intermediate 7.i (0.8 g, 1.91 mmol), the title compound was obtained as a yellowish foam (0.175 g, 29% yield) using the procedure of Example 1, step 1.iii.

MS (ESI, m/z): 318.1 [M+H$^+$] for $C_{17}H_{23}N_3O_3$.

7. iii. 1-((2R)-2-{4-[(2,3-dihydro-[1, 4]dioxino[2,3-c]pyridin-7-ylmethyl)-amino]-cyclohexyl}-2-hydroxy-ethyl)-7-methoxy-1H-quinoxalin-2-one Starting from intermediate 7.ii (0.193 g, 0.608 mmol) and 2,3-dihydro-[1,4]dioxino[2,3-c]pyridine-7-carbaldehyde (0.101 g, 1 eq.), the title compound was obtained as an off-white foam (0.178 g, 63% yield) using the procedure of Example 1, step 1.1v. The crude material was purified by CC (DCM-MeOH 93:7 containing 0.7% aq. NH$_4$OH).

$^1$H NMR (d$_6$DMSO) δ: 8.03 (s, 1H); 8.01 (s, 1H); 7.73 (d, J=8.8 Hz, 1H); 7.08 (d, J=2.5 Hz, 1H); 6.98 (dd, J=2.5, 8.8 Hz, 1H); 4.76 (d, J=5.8 Hz, 1H); 4.32-4.36 (m, 2H); 4.28-4.30 (m, 2H); 4.25 (partially overlapped dd, J=3.5, 14.1 Hz, 1H); 4.16 (dd, J=9.0, 14.1 Hz, 1H); 3.89 (s, 3H); 3.69 (s, 2H); 3.63 (m, 1H); 2.32 (m, 1H); 2.07 (br. s, 1H); 1.88-1.99 (m, 4H); 1.72 (m, 1H); 1.41 (m, 1H); 0.97-1.27 (m, 4H).

MS (ESI, m/z): 467.2 [M+H$^+$] for $C_{25}H_{30}N_4O_5$.

Example 8

1-((2S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-7-methoxy-1H-[1,8]naphthyridin-2-one Starting from intermediate 1.ii (0.1 g, 0.31 mmol) and 6,7-dihydro-8-oxa-5-thia-1,2-diaza-naphthalene-3-carbaldehyde (0.057 g, 1 eq., prepared according to WO 2009/000745), the title compound was obtained as a white foam (0.020 g, 14% yield) using the procedure of Example 1, step 1.iii. The crude material was purified by CC (DCM-MeOH 93:7 containing 0.7% aq. NH$_4$OH).

$^1$H NMR (d6DMSO) δ: 8.01 (d, J=8.5 Hz, 1H); 7.82 (d, J=9.4 Hz, 1H); 7.52 (s, 1H); 6.68 (d, J=8.5 Hz, 1H); 6.46 (d, J=9.4 Hz, 1 H); 4.64 (dd, J=8.5, 12.6 Hz, 1H); 4.53-4.59 (m, 2H); 4.37 (d, J=6.7 Hz, 1H); 4.31 (dd, J=3.8, 12.6 Hz, 1H); 3.88-3.94 (m, 2H); 3.93 (s, 3H); 3.78-3.83 (m, 2H), 3.25-3.31 (m, 2H); 3.17 (m, 1H); 2.88 (t, J=10.3 Hz, 1H); 2.43 (m, 1H); 2.21 (m, 1H); 1.99 (m, 1H); 1.47-1.62 (m, 2H); 1.17 (m, 1H).

MS (ESI, m/z): 486.4 [M+H$^+$] for $C_{23}H_{27}N_5O_5S$.

Example 9

1-((2S)-2-hydroxy-2-{(2S,5R)-5-[(3-oxa-1-thia-5-aza-indan-6-ylmethyl)-amino]-tetrahydro-pyran-2-yl}-ethyl)-7-methoxy-1H-[1,8]naphthyridin-2-one Starting from intermediate 1.ii (0.884 g, 2.77 mmol) and [1,3]oxathiolo[5,4-c]pyridine-6-carbaldehyde (prepared as described in WO 2006/002047; 0.463 g, 1 eq.), the title compound was obtained as a white foam (0.5 g, 38% yield) using the procedure of Example 1, step 1.iii. The crude material was purified by CC (DCM-MeOH 93:7 containing 0.7% aq. NH$_4$OH).

$^1$H NMR (d6DMSO) δ: 8.01 (d, J=8.5 Hz, 1H); 7.96 (s, 1H); 7.82 (d, J=9.4 Hz, 1H); 7.40 (s, 1H); 6.68 (d, J=8.5 Hz, 1H); 6.46 (d, J=9.4 Hz, 1H); 5.81 (s, 2H); 4.65 (dd, J=9.1, 12.9 Hz, 1H); 4.36 (d, J=6.7 Hz, 1H); 4.31 (dd, J=4.4, 12.9 Hz, 1H); 3.90-3.93 (m, 2H); 3.93 (s, 3H); 3.63-3.74 (m, 2H), 3.16 (m, 1H); 2.88 (t, J=10.5 Hz, 1H); 2.43 (m, 1H); 1.95-2.08 (m, 2H); 1.44-1.65 (m, 2H); 1.19 (m, 1H).

MS (ESI, m/z): 471.3 [M+H$^+$] for $C_{23}H_{26}N_4O_5S$.

Example 10

3-fluoro-1-((2S)-2-hydroxy-2-{(2S,5R)-5-[(3-oxa-1-thia-5-aza-indan-6-ylmethyl)-amino]-tetrahydro-pyran-2-yl}-ethyl)-7-methoxy-1H-[1,8]naphthyridin-2-one

10.i. 7-chloro-3-fluoro-1,8-naphthyridin-2(1H)-one

To a solution of N-(6-chloro-3-formylpyridin-2-yl)pivalamide (prepared as described in *J. Org. Chem.* (1990), 55, 4744; 3.0 g, 12.64 mmol) in MeCN (250 mL) was added triethyl 2-fluoro-phosphonoacetate (4 g, 16.51 mmol), lithium chloride (0.935 g) and DBU (2.8 mL, 18.7 mmol). The mixture was stirred at rt for 4 h. The solvent was evaporated and the residue was partitioned between 1N HCl (100 mL) and ether (150 mL). The aq. layer was extracted with ether (100 mL) and the combined ethereal layers were dried over Na$_2$SO$_4$, filtered and concentrated to dryness. The residue was taken up in dioxane (15 mL) and 6N HCl (50 mL) was added. The mixture was heated to reflux for 90 min. The mixture was cooled to 0° C. and the volatiles were removed in vacuo. The solids were filtered off and washed with water. The solid was dried in vacuo to afford the title compound as a yellow solid (1.38 g, 56% yield). The title compound was only 70% pure.

MS (ESI, m/z): 199.1 [M+H$^+$] for $C_8H_4N_2OClF$.

10.ii. 3-fluoro-7-methoxy-1,8-naphthyridin-2(1H)-one

A solution of the intermediate 10.i (1.38 g, 6.95 mmol) in a solution of MeONa in MeOH (25 wt %, 40 mL) was heated to reflux for 90 min. The reaction mixture was cooled to 0° C. and 2N HCl (10 mL) was added. The volatiles were removed in vacuo and the residue was filtered. The solids were dried in vacuo to afford the title compound as a beige solid (1.0 g, 74% yield). The title compound was only 75% pure.

MS (ESI, m/z): 195.2 [M+H$^+$] for $C_9H_7N_2O_2F$.

10.iii. 1-((2 S)-2-((2 S, 5R)-5-aminotetrahydro-2H-pyran-2-yl)-2-hydroxyethyl)-3 fluoro-7-methoxy-1, 8-naphthyridin-2(1H)-one Starting from the intermediate 10.ii (1.0 g) and the compound of Preparation A (1.51 g, 6.24 mmol), the title amine (0.13 g) was obtained as a white solid using the procedures of Example 1, steps 1.i (epoxide opening, 7% yield) and 1.ii (Boc deprotection, 94% yield). If necessary, the crude reaction mixtures were purified by CC using an appropriate mixture of solvents.

$^1$H NMR (CDCl$_3$) δ: 7.73 (d, J=8.5 Hz, 1H); 7.35 (d, J=8.8 Hz, 1H); 6.69 (d, J=8.5 Hz, 1H); 4.90 (dd, J=9.0, 13.2 Hz,

1H); 4.67 (dd, J=4.2, 13.2 Hz, 1H); 3.93-4.03 (m, 2H); 4.01 (s, 3H); 3.38 (dt, J=2.9, 10.8 Hz, 1H); 3.04 (t, J=10.5 Hz, 1H); 2.82 (m, 1H); 2.09 (m, 1H); 1.65-1.86 (m, 2H); 1.36 (br. s, 3H); 1.27 (m, 1H).

MS (ESI, m/z): 338.3 [M+H$^+$] for $C_{16}H_{20}N_3O_4F$.

10.iv. 3-fluoro-1-((2 S)-2-hydroxy-2-{(2S,5R)-5-[(3-oxa-1-thia-5-aza-indan-6-ylmethyl)-amino]tetrahydro-pyran-2-yl}-ethyl)-7-methoxy-1H-[1,8]naphthyridin-2-one Starting from intermediate 10.iii (0.130 g, 0.407 mmol) and [1,3]oxathiolo[5,4-c]pyridine-6-carbaldehyde (0.068 g. 1.0 eq.), the title compound was obtained as a white foam (0.03 g, 15% yield) using the procedure of Example 1, step 1.iii. The crude material was purified by CC (DCM-MeOH 93:7 containing 0.7% aq. NH$_4$OH).

$^1$H NMR (d6DMSO) δ: 8.01 (d, J=8.5 Hz, 1H); 7.97 (s, 1H); 7.83 (d, J=10.0 Hz, 1H); 7.41 (s, 1H); 6.76 (d, J=8.5 Hz 1H); 5.80 (s, 2H); 4.72 (dd, J=9.0, 12.6 Hz, 1H); 4.48 (d, J=6.4 Hz, 1H); 4.31 (dd, J=4.1, 12.6 Hz, 1H); 3.89-3.97 (m, 2H); 3.93 (s, 3H); 3.64-3.74 (m, 2H); 3.19 (m, 1H); 2.90 (t, J=10.5 Hz, 1H); 2.43 (overlapped m, 1H); 2.01 (m, 1H); 1.90 (m, 1H); 11.44-1.63 (m, 2H); 1.18 (m, 1H).

MS (ESI, m/z): 489.5 [M+H$^+$] for $C_{23}H_{25}N_4O_5FS$.

Example 11

4-((2S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-6-methoxy-4H-pyrido[2,3-b]pyrazin-3-one

11.i. 4-((2S)-2-((2S,5R)-5-aminotetrahydro-2H-pyran-2-yl)-2-hydroxyethyl)-6-methoxypyrido[2,3-b]pyrazin-3(4H)-one Starting from 6-methoxypyrido[2,3-b]pyrazin-3(4H)-one. (prepared as described inWO 2008/128942; 1.58 g, 8.97 mmol) and the compound of Preparation A (2.35 g, 9.68 mmol), the title amine was obtained as a white solid (2.41 g) using the procedures of Example 1, steps 1.i (epoxide opening, 48% yield) and 1.ii (Boc deprotection, 91% yield). If necessary, the crude reaction mixtures were purified by CC using an appropriate mixture of solvents.

MS (ESI, m/z): 321.3[M+H$^+$] for $C_{15}H_{20}N_4O_4$.

11. ii. 4-((2S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-6-methoxy-4H-pyrido[2,3-b]pyrazin-3-one Starting from intermediate 11.i (0.160 g, 0.5 mmol) and 2,3-dihydro-[1,4]oxathiino[2,3-c]pyridine-7-carbaldehyde (0.092 g. 1.0 eq.), the title compound was obtained as a yellow solid (0.035 g, 15% yield) using the procedure of Example 1, step 1.iii. The crude material was purified by CC (DCM-MeOH 93:7 containing 0.7% aq. NH$_4$OH). The compound was further triturated in TBME.

$^1$H NMR (d6DMSO) δ: 8.09 (d, J=8.5 Hz, 1H); 8.07 (s, 1H); 7.92 (s, 1H); 7.13 (s, 1H); 6.79 (d, J=8.5 Hz, 1H); 4.59-4.63 (m, 2H); 4.33-4.38 (m, 2H); 4.21 (dd, J=3.8, 12.3 Hz, 1H); 3.87-4.01 (m, 2H); 3.95 (s, 3H); 3.59-3.70 (m, 2H); 3.21-3.26 (m, 2H); 3.21 (overlapped m, 1H); 2.89 (t, J=10.5 Hz, 1H); 2.42 (m, 1H); 1.95-2.07 (m, 2H); 1.43-1.64 (m, 2H); 1.18 (m, 1H).

MS (ESI, m/z): 486.4 [M+H$^+$] for $C_{23}H_{27}N_5O_5S$.

Example 12

4-((2S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-6-methoxy-4H-pyrido[2,3-b]pyrazin-3-one

12.i. 4-((2S)-2-((2S,5R)-5-(((6,7-dihydro-[1,4]oxathiino[2,3-c]pyridazin-3-yl)methyl)amino)tetrahydro-2H-pyran-2-yl)-2-hydroxyethyl)-6-methoxy-1,2-dihydropyrido[2,3-b]pyrazin-3(4H)-one Starting from intermediate 11.i (0.205 g, 0.644 mmol) and 6,7-dihydro-8-oxa-5-thia-1,2-diaza-naphthalene-3-carbaldehyde (0.119 g. 1.0 eq.), the title compound was obtained as a yellow solid (0.120 g, 38% yield) using the procedure of Example 1, step 1.iii. The crude material was purified by CC (DCM-MeOH 93:7 containing 0.7% aq. NH$_4$OH). The compound was further triturated in TBME.

MS (ESI, m/z): 489.6 [M+H$^+$] for $C_{22}H_{28}N_6O_5S$.

12.ii. 4-((2S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-6-methoxy-4H-pyrido[2,3-b]pyrazin-3-one To a solution of the intermediate 12.i (0.1 g, 0.226 mmol) in DCM (2.5 mL) and MeOH (0.5 mL) was added MnO$_2$ (0.039 g, 0.451 mmol). The mixture was stirred at rt for 1.5 h. The reaction mixture was filtered and the filtrate was concentrated to dryness. The residue was purified by CC (DCM-MeOH 93:7 containing 0.7% aq. NH$_4$OH) to afford the title compound as a yellowish foam (0.076 g, 70% yield).

$^1$H NMR (d6DMSO) δ: 8.09 (d, J=8.5 Hz, 1H); 8.07 (s, 1H); 7.53 (s, 1H); 6.79 (d, J=8.5 Hz, 1H); 4.53-4.63 (m, 4H); 4.21 (dd, J=4.1, 12.6 Hz, 1H); 3.87-4.01 (m, 2H); 3.95 (s, 3H); 3.76-3.86 (m, 2H); 3.25-3.30 (m, 2H); 3.21 (m, 1H); 2.89 (t, J=10.3 Hz, 1H); 2.42 (m, 1H); 1.95-2.07 (m, 2H); 1.43-1.64 (m, 2H); 1.18 (m, 1H).

MS (ESI, m/z): 487.56 [M+H$^+$] for $C_{22}H_{26}N_6O_5S$.

Example 13

5-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-3-methoxy-5H-pyrido[2,3-b]pyrazin-6-one

13.i. 5-((2S)-2-((2S,5R)-5-aminotetrahydro-2H-pyran-2-yl)-2-hydroxyethyl)-3-methoxypyrido[2,3-b]pyrazin-6(5H)-one Starting from 3-methoxypyrido[2,3-b]pyrazin-6(5H)-one (prepared as described in WO 2009/087153; 0.6 g, 3.40 mmol) and the compound of Preparation A (0.83 g, 3.40 mmol), the title amine was obtained as a yellowish foam (0.173 g) using the procedures of Example 1, steps 1.i (epoxide opening, 80% yield) and 1.ii (Boc deprotection, 21% yield). If necessary, the crude reaction mixtures were purified by CC using an appropriate mixture of solvents.

$^1$H NMR (d6DMSO) δ:8.18 (s, 1H); 7.90 (d, J=9.7 Hz, 1H); 6.68 (d, J=9.7 Hz, 1H); 4.62 (dd, J=8.8, 12.9 Hz, 1H); 4.48 (br. d, J=5.9 Hz, 1H); 4.25 (dd, J=4.4, 12.9 Hz, 1H); 4.01 (s, 3H); 3.91 (m, 1H); 3.76 (m, 1H); 3.14 (m, 1H); 2.80 (t, J=10.5 Hz, 1H); 2.55 (m, 1H); 1.89 (m, 1H); 1.50-1.68 (m, 4H); 1.14 (m, 1H).

MS (ESI, m/z): 321.1 [M+H$^+$] for $C_{15}H_{20}N_4O_4$.

13. ii. 5-((2S)-2-{(2S,5R)-5-[(2,3-dihydro-[1,4]dioxino[2,3-c]pyridin-7-ylmethyl)-amino]-tetrahydropyran-2-yl}-2-hydroxy-ethyl)-3-methoxy-5H-pyrido[2,3-b]pyrazin-6-one Starting from intermediate 13.i (0.084 g, 0.261 mmol) and 2,3-dihydro-[1,4]dioxino[2,3-c]pyridine-7-carbaldehyde (0.043 g. 1.0 eq.), the title compound was obtained as a yellowish foam (0.057 g, 47% yield) using the procedure of Example 1, step 1.iii. The crude material was purified by CC (DCM-MeOH 93:7 containing 0.7% aq. $NH_4OH$).

$^1H$ NMR (d6DMSO) δ: 8.17 (s, 1H); 7.98 (s, 1H); 7.90 (d, J=9.7 Hz, 1H); 6.90 (s, 1H); 6.68 (d, J=9.7 Hz, 1H); 4.61 (dd, J=8.8, 12.6 Hz, 1H); 4.48 (d, J=6.7 Hz, 1H); 4.30-4.34 (m, 2H); 4.24-4.28 (m, 2H); 4.24 (dd, J=4.1, 12.6 Hz, 1H); 3.99 (s, 3H); 3.93-3.85 (m, 2H); 3.60-3.70 (m, 2H); 3.18 (m, 1H); 2.88 (t, J=10.5 Hz, 1H); 2.41 (m, 1H); 2.06 (br. s, 1H); 1.99 (m, 1H); 1.44-1.62 (m, 2H); 1.19 (m, 1H).

MS (ESI, m/z): 470.2 [M+H$^+$] for $C_{23}H_{27}N_5O_6$.

Example 14

5-((2S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-3-methoxy-5H-pyrido[2,3-b]pyrazin-6-one Starting from intermediate 13.i (0.096 g, 0.3 mmol) and 2,3-dihydro-[1,4]oxathiino[2,3-c]pyridine-7-carbaldehyde (0.055 g. 1.0 eq.), the title compound was obtained as a yellowish foam (0.080 g, 55% yield) using the procedure of Example 1, step 1.iii. The crude material was purified by CC (DCM-MeOH 93:7 containing 0.7% aq. $NH_4OH$).

MS (ESI, m/z): 486.3 [M+H$^+$] for $C_{23}H_{27}N_5O_5S$.

Example 15

5-((S)-2-{(2S,5R)-5-[(6,7-dihydro-8-oxa-5-thia-1,2-diaza-naphthalen-3-ylmethyl)-amino]-tetrahydropyran-2-yl}-2-hydroxy-ethyl)-3-methoxy-5H-pyrido[2,3-b]pyrazin-6-one Starting from intermediate 13.i (0.115 g, 0.36 mmol) and 6,7-dihydro-[1,4]oxathiino[2,3-c]pyridazine-3-carbaldehyde (0.066 g. 1.0 eq.), the title compound was obtained as a yellowish foam (0.056 g, 32% yield) using the procedure of Example 1, step 1.iii. The crude material was purified by CC (DCM-MeOH 93:7 containing 0.7% aq. $NH_4OH$).

$^1H$ NMR (d6DMSO) δ: 8.17 (s, 1H); 7.90 (d, J=9.7 Hz, 1H); 7.52 (s, 1H); 6.68 (d, J=9.7 Hz, 1H); 4.61 (overlapped dd, J=8.8, 12.6 Hz, 1H); 4.55-4.58 (m, 2H); 4.49 (d, J=6.7 Hz, 1H); 4.24 (dd, J=4.1, 12.6 Hz, 1H); 3.99 (s, 3H); 3.85-3.94 (m, 2H); 3.75-3.85 (m, 2H); 3.25-3.31 (m, 2H); 3.17 (m, 1H); 2.87 (t, J=10.5 Hz, 1H); 2.40 (m, 1H); 2.21 (m, 1H); 1.99 (m, 1H); 1.45-1.61 (m, 2H); 1.18 (m, 1H).

MS (ESI, m/z): 487.6 [M+H$^+$] for $C_{22}H_{26}N_6O_5S$.

Pharmacological Properties of the Invention Compounds
In Vitro Assays
1) Bacterial Growth Minimal Inhibitory Concentrations:
Experimental Methods:

Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:
All Example compounds were tested against several Gram positive and Gram negative bacteria.
Typical antibacterial test results are given in Table 1 hereafter (MIC in mg/l).

TABLE 1

| Example No. | MIC for S. aureus 29213 | Example No. | MIC for S. aureus 29213 |
|---|---|---|---|
| 1 | ≤0.031 | 2 | ≤0.031 |
| 3 | ≤0.031 | 4 | ≤0.031 |
| 5 | 0.063 | 6 | ≤0.031 |
| 7 | ≤0.031 | 8 | 0.5 |
| 9 | ≤0.031 | 10 | ≤0.031 |
| 11 | ≤0.031 | 12 | 0.063 |
| 13 | 0.125 | 14 | ≤0.031 |
| 15 | 0.25 | | |

2) In Vitro Blocking of hERG K$^+$ Channels:
Principle:

Drug-induced prolongation of the QT interval and resultant ventricular dysrhythmia, including torsades de pointes, is an adverse event which occurs among other drugs, within some members of various classes of anti-infective agents. During recent years, there have been numerous antibacterials either withdrawn from the market or abandoned in various phases of clinical development due to their potential to cause this life-threatening toxicity. Anti-infective agents warrant particular attention, as these are used in rather high concentrations and frequently added to complicated drug regimens when complete information regarding a drug regimen may be lacking Certain anti-infective drug classes, such as the macrolides and quinolones as well as the recently disclosed Viquidacin which belongs to the same chemical classes as the compounds of the present invention, have all been implicated. In fact, the ability to prolong the QT interval often varies among members of these drug classes and the potential for this effect cannot be predicted accurately during drug design and development. The best predictor is the extent of the hERG K$^+$ channel blockade. Although some predictive models for hERG inhibition have been developed, there is today no clear Structure-Activity Relationship to predict such an inhibition. We have discovered that combining two features of the present invention leads to compounds with reduced hERG liabilities while maintaining the level of antibacterial activity.

Experimental Methods:

hERG K$^+$ channels have been cloned from human heart and recombinant channels are stably expressed in CHO-K1 cells (CHO$_{hERG}$). These cells have been purchased from bSys GmbH(CH-4052 Basel, Switzerland) and are grown in 150 mL culture flasks at 37° C. in 5% CO$_2$. When the cells are ~100% confluent, they are detached with 0.25% trypsin-EDTA solution and placed in the cell preparation unit of a QPatch automated patch-clamp robot (Sophion Bioscience A/S, 2750 Ballerup, Denmark).

Currents through the hERG K$^+$ channels (IK$_{hERG}$) are elicited using the following buffer solutions and voltage protocol:
  extracellular solution (in mM): [NaCl]=150; [KCl]=4; [CaCl$_2$]=1.2; [MgCl$_2$]=1; [HEPES]=10; pH adjusted to 7.4 with NaOH;
  intracellular solution (in mM): [KCl]=140; [NaCl]=10; [MgCl$_2$]=1; [HEPES]=10; [EGTA]=5; [Mg-ATP]=5; [Na$_3$-GTP]=0.1; pH adjusted to 7.2 with KOH;
  voltage protocol: the resting potential is −80 mV and the frequency of stimulation is 0.1 Hz. hERG K$^+$ currents are measured as the average current during the last 20 ms of the 500 ms pulse to −40 mV minus the average current during the last 20 ms of the 50 ms pulse to −40 mV.

After the cells have stabilized for a few minutes and the currents are steady, the amplitude of $IK_{hERG}$ is recorded under control conditions. Thereafter, the QPatch robot applies the test compound to the cell at the test concentration and, after 4 minutes of stimulation, the amplitude of $IK_{hERG}$ is recorded under test conditions. The ratio of the two amplitudes is used to define a fractional block and the average block on two cells is used to provide the effect of a given concentration (e.g. 10 µM). If, for a given test compound, a sufficient number of concentrations were tested, an apparent $IC_{50}$ for inhibition of $IK_{hERG}$ is calculated.

Results:

Testing the compounds having the formula $I_{COMP}$ shown below $I_{COMP}$ using the experimentals methods described above for the MIC regarding *S. aureus* A798 bacteria and for in vitro blocking hERG K⁺ channels gave the results summarised in the Table 2 hereafter.

TABLE 2

| Example No. or Reference Example No. | U | W | A | R³ | X | MIC for S. aureus A798 | % inhibition hERG (at 10 µM) |
|---|---|---|---|---|---|---|---|
| Example No. 2 | N | CH | O | OH | N | ≦0.063 | 18 |
| Example No. 3 | CH | N | O | OH | N | ≦0.063 | 18 |
| Example No. 4 | N | N | O | OH | N | ≦0.063 | 7 |
| Example No. 6 | N | CH | CH | OH | N | ≦0.063 | 35 |
| Example No. 7 | CH | N | CH | OH | N | 0.125 | 18 |
| Reference Example No 1 | N | CH | O | OH | CH | ≦0.063 | 74 |
| Example No. 388 of WO 2006/137485 | CH | N | CH | H | N | ≦0.063 | 75 |

Other Example compounds were also tested for in vitro blocking hERG K⁺ channels. The results of these tests are gathered in Table 3 hereafter

TABLE 3

| Example No. | % inhibition hERG (at 10 µM) | Example No. | % inhibition hERG (at 10 µM) |
|---|---|---|---|
| 1 | 32 | 5 | 28 |
| 8 | 6 | 9 | 52 |
| 10 | 48 | 11 | 45 |
| 12 | 7 | 13 | 5 |
| 15 | 0 | | |

The invention claimed is:

1. A compound of formula I

I wherein
$R^1$ represents alkoxy;
each of U and V represents CH and W represents CH, or
U represents N, V represents CH and W represents CH, or
each of U and V represents N and W represents CH;
$R^2$ represents hydrogen or fluorine;
A represents O or $CH_2$;
Y represents CH or N;
Q represents O or S; and
n represents 0 or 1;
or a salt of the compound.

2. The compound according to claim 1, which is also a compound of formula $I_p$ $I_p$ wherein
$R^1$ represents alkoxy;
U represents CH or N and W represents CH;
A represents O or $CH_2$;
Y represents CH or N; and
Q represents O or S;
or a salt of the compound.

3. The compound according to claim 1, wherein Y represents CH;
or a salt of the compound.

4. The compound according to claim 1, wherein Q represents O;
or a salt of the compound.

5. The compound according to claim 1, wherein $R^1$ represents methoxy; or a salt of the compound.

6. The compound according to claim 1, wherein A represents O; or a salt of the compound.

7. The compound according to claim 1, wherein A represents $CH_2$;
or a salt of the compound.

8. The compound according to claim 1, wherein n represents 1; or a salt of the compound.

9. The compound according to claim 1, wherein:
R¹ represents methoxy;
U represents N and V represents N and W represents CH;
R² represents hydrogen;
A represents O or CH₂;
Y represents CH;
Q represents O or S; and
n represents 1;
or a salt of the compound.

10. The compound according to claim 1, which is selected from:
- 1-((S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-7-methoxy-1H-[1,8]naphthyridin-2-one;
- 1-((2S)-2-{(2S,5R)-5-[(2,3-dihydro-[1,4]dioxino[2,3-c]pyridin-7-ylmethyl)-amino]-tetrahydro-pyran-2-yl}-2-hydroxy-ethyl)-7-methoxy-1H-[1,8]naphthyridin-2-one;
- 1-((2S)-2-{(2S,5R)-5-[(6,7-dihydro-[1,4]dioxino[2,3-c]pyridazin-3-ylmethyl)-amino]-tetrahydro-pyran-2-yl}-2-hydroxy-ethyl)-7-methoxy-1H-[1,8]naphthyridin-2-one;
- 1-(2R)-2-{4-[(2,3-dihydro-[1,4]dioxino[2,3-c]pyridin-7-ylmethyl)-amino]-cyclohexyl}-2-hydroxy-ethyl)-7-methoxy-1H-[1,8]naphthyridin-2-one;
- 1-((2S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-7-methoxy-1H-[1,8]naphthyridin-2-one;
- 1-(2S)-2-hydroxy-2-{(2S,5R)-5-[(3-oxa-1-thia-5-aza-indan-6-ylmethyl)-amino]-tetrahydro-pyran-2-yl}-ethyl)-7-methoxy-1H-[1,8]naphthyridin-2-one
- 3-fluoro-1-((2S)-2-hydroxy-2-{(2S,5R)-5-[(3-oxa-1-thia-5-aza-indan-6-ylmethyl)-amino]-tetrahydro-pyran-2-yl}-ethyl)-7-methoxy-1H-[1,8]naphthyridin-2-one;
- 5-((2S)-2-{(2S,5R)-5-[(2,3-dihydro-[1,4]dioxino[2,3-c]pyridin-7-ylmethyl)-amino]-tetrahydro-pyran-2-yl}2-hydroxy-ethyl)-3-methoxy-5H-pyrido[2,3-b]pyrazin-6-one;
- 5-(2S)-2-{(2S,5R)-5-[(2,3-dihydro-4-oxa-1-thia-6-aza-naphthalen-7-ylmethyl)-amino]-tetrahydro-pyran-2-yl}-2-hydroxy-ethyl)-3-methoxy-5H-pyrido[2,3-b]pyrazin-6-one; or
- 5-((S)-2-{(2S,5R)-5-[(6,7-dihydro-8-oxa-5-thia-1,2-diaza-naphthalen-3-ylmethyl)-amino]-tetrahydro-pyran-2-yl}-2-hydroxy-ethyl)-3-methoxy-5H-pyrido[2,3-b]pyrazin-6-one;

or a salt of the compound.

11. A medicament comprising the compound according to claim 1, or a pharmaceutically acceptable salt thereof.

12. A pharmaceutical composition comprising as an active principal, the compound according to claim 1, or a pharmaceutically acceptable salt thereof, and at least one therapeutically inert excipient.

* * * * *